(12) United States Patent
Kao et al.

(10) Patent No.: US 8,025,901 B2
(45) Date of Patent: Sep. 27, 2011

(54) BIFUNCTIONAL-MODIFIED HYDROGELS

(75) Inventors: Weiyuan John Kao, Middleton, WI (US); Jing Li, Madison, MN (US); David Lok, Madison, WI (US); Rathna Gundloori, Maharastra (IN)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 12/615,859

(22) Filed: Nov. 10, 2009

(65) Prior Publication Data

US 2010/0209509 A1 Aug. 19, 2010

Related U.S. Application Data

(63) Continuation of application No. 10/128,198, filed on Apr. 23, 2002, now Pat. No. 7,615,593.

(60) Provisional application No. 60/285,782, filed on Apr. 23, 2001.

(51) Int. Cl.
| A61K 35/00 | (2006.01) |
| A61K 9/10 | (2006.01) |
| A61K 47/48 | (2006.01) |
| C08G 81/00 | (2006.01) |
| C08L 101/00 | (2006.01) |
| C08L 101/14 | (2006.01) |

(52) U.S. Cl. .............. 424/484; 424/486; 514/772.1; 514/774; 435/177; 523/113; 530/815; 530/817

(58) Field of Classification Search ............ 424/484, 424/486; 514/772.1, 774; 435/177; 523/113; 530/815, 817
See application file for complete search history.

(56) References Cited

U.S. PATENT DOCUMENTS

| 4,390,519 | A | 6/1983 | Sawyer | |
| 5,153,265 | A | 10/1992 | Shadle et al. | |
| 5,672,662 | A | 9/1997 | Harris et al. | |
| 5,847,089 | A | 12/1998 | Damodaran et al. | |
| 5,863,984 | A | 1/1999 | Doillon et al. | |
| 5,904,927 | A | 5/1999 | Amiji | |
| 6,043,328 | A | 3/2000 | Domschke et al. | |
| 6,129,761 | A | 10/2000 | Hubbell | |
| 6,132,765 | A | 10/2000 | DiCosmo et al. | |
| 6,258,351 | B1 | 7/2001 | Harris | |
| 6,310,105 | B1 | 10/2001 | Damodaran | |
| 6,323,278 | B2 | 11/2001 | Rhee et al. | |
| 6,348,558 | B1 * | 2/2002 | Harris et al. | 528/196 |
| 6,730,299 | B1 | 5/2004 | Tayot et al. | |
| 6,818,018 | B1 | 11/2004 | Sawhney | |
| 7,615,593 | B2 | 11/2009 | Kao et al. | |
| 2005/0276858 | A1 | 12/2005 | Kao et al. | |
| 2006/0100369 | A1 | 5/2006 | Kao et al. | |

FOREIGN PATENT DOCUMENTS

| EP | 747066 | 12/1996 |
| JP | 6-503840 | 4/1994 |
| JP | 8-231435 | 9/1996 |
| JP | 9-99052 | 4/1997 |
| JP | 10-085318 | 4/1998 |
| WO | WO 90/05755 | 5/1990 |
| WO | WO 93/00890 | 1/1993 |
| WO | WO 96/40304 | 12/1996 |
| WO | WO 96/40817 | 12/1996 |
| WO | WO 97/03106 | 1/1997 |
| WO | WO 97/22371 | 6/1997 |
| WO | WO 98/28364 | 7/1998 |
| WO | WO 98/46287 | 10/1998 |
| WO | WO 99/22770 | 5/1999 |
| WO | WO 00/78846 | 12/2000 |
| WO | WO 01/05443 | 1/2001 |
| WO | WO 02/085419 | 10/2002 |

OTHER PUBLICATIONS

Abuchowski et al., "Cancer therapy with chemically modified enzymes. I. Antitumor properties of polyethylene glycol—asparaginase conjugates," Cancer Biochem. Biophys. (1984) 7:175-186.

Andreopoulos, F.M. et al., "Photoimmobilization of organophosphorus hydrolase within a PEG-based hydrogel," Biotechnol. Bioeng. (1999) 65:579-588.

Brown et al., "The structure of propadienone," J. Am. Chem. Soc. (1985) 107:4109.

Bruson, "Cyanoethylation," Organic Reactions (1949) 5:79.

Buckmann et al., "Functionalization of poly(ethylene glycol) and monomethoxy-poly(ethylene glycol)," Markromol. Chem. (1981) 182:1379-1384.

Burmania et al., "Protein-based interpenetrating networks (IPN) for tissue scaffolds/drug release," (May 2, 2002).

Delgado et al., "The uses and properties of PEG-linked proteins," Crit. Rev. Ther. Drug Carrier System. (1992) 9:249.

Druniheller et al., "Densely crosslinked polymer networks of poly-(ethylene glycol) in trimethylolpropane triacrylate for cell-adhesion-resistant surfaces," J. Biomed. Mater. Res. (1995) 29:207.

D'Urso, E.M. et al., "Albumin-poly(ethylene glycol) hydrogel as matrix for enzyme immobilization: biochemical characterization of crosslinked acid phosphatase," Enz. Micro. Tech. (1996) 18:482-488.

Einerson et al., "Synthesis and physiochemical analysis of gelatin-based hydrogels for cell/drug carrier matrices," (May 2, 2002).

Fortier, "New polyethylene glycols for biomedical applications," Biotechnol. Genet. Eng. Rev. (1994) 12:329.

Harris et al., "Introduction to chemistry and biological applications of poly(ethylene glycol)," Am. Chem. Soc. Polymer Preprints (1989) 30:356.

Harris, J.M. et al., "Poly(ethylene glycol) chemistry and biological applications," Amer. Chemical Society, Washington, D.C. (1997) (Book).

(Continued)

Primary Examiner — Nathan M Nutter
(74) Attorney, Agent, or Firm — Foley & Lardner LLP

(57) ABSTRACT

Disclosed are hydrogels wherein a polymer matrix is modified to contain a bifunctional poly(alkylene glycol) molecule covalently bonded to the polymer matrix. The hydrogels can be cross-linked using, for example, glutaraldehyde. The hydrogels may also be crosslinked via an interpenetrating network of a photopolymerizable acrylates. The hydrogels may also be modified to have pharmacologically-active agents covalently bonded to the poly(alkylene glycol) molecules or entrained within the hydrogel. Living cells may also be entrained within the hydrogels.

17 Claims, 6 Drawing Sheets

OTHER PUBLICATIONS

Hern et al., "Incorporation of adhesion peptides into nonadhesive hydrogels useful for tissue resurfacing," J. Biomed. Mater. Res. (1998) 39:2666-2676.

Inada et al., "Biomedical and biotechnological applications of PEG- and PM-modified proteins," Trends Biotechnol. (1995) 13:86.

Kao et al., "Engineering endogenous inflammatory cells as delivery vehicles," J. Controlled Release (2002) 78:219-233.

Kao et al., "Evaluation of protein-modulated macrophage behavior on biomaterials: designing biomimetric materials for cellular engineering," Biomaterials (1999) 20:2213-2221.

Kao et al., "In vivo modulation of host response and macrophage behavior by polymer networks grafted with fibronectin-derived biomimetric oligopeptides: the role of RGD and PHSRN domains," Biomaterials (2001) 22:2901-2909.

Kao et al., "Murine macrophage behavior on peptide-grafted polyethylenoglycol-containing networks," Biotech. Bioengin. (1998) 59:2-9.

Kao et al., "Preparation of heterodifunctional polyethyleneglycols: network formatino, characterization and cell culture analysis," J. Biomataer, Sci. Polymer Edn (2001) 12(6):599-611.

Kao et al., "Role for interleukin-4 in foreign-body giant cell formation on a poly(etherurethane urea) in vivo," J. Biomed. Mater. Res. (1995) 29(10):1267-1275.

Kao et al., "Theoretical analysis of in vivo macrophage adhesion and foreign body giant cell formation on polydimethylsiloxane, low density polyethylene and polytheruretanes," J. Biomed. Mater. Res. (1994) 28:73-79.

Kao et al., "Theoretical analysis of in vivo macrophage and foreign body giant cell formation on strained poly(etherurethane urea) elastomers," J. Biomed. Mater. Res. (1994) 2:819-829.

Kao et al., "Utilizing biomimetric oligopeptides to probe fibronectin-integrin binding and signaling in regulating macrophage function in vitro and in vivo," Frontiers in Biosciences (2001) 6:D992-999.

Kao et al., Handbook of Biomaterial Evaluation, 2nd Edition, Taylor & Frances Publishing, Philadelphia, PA (1999) 659-669.

Kao, W.J. et al., Fibronectin modulates macrophage adhesion and FBGC formation: the role of RGD, PHSRN, J. Biomed. Mater. Res. (2001) 55(1):79-88 (Duplicate of online publication above).

Liu et al., "Human macrophage adhesion on fibronectin: the role of substratum and intracellular signalling kinases," Cellular Signalling (2002) 14:145-152.

Llanos, G.R. et al., "Immobilization of poly(ethylene glycol) onto a poly(vinyl alcohol) hydrogel 1: Synthesis and characterization," Macromolecules (1991) 24:6065-6072.

Llanos, G.R. et al., "Heparin-poly(ethylene glycol)-poly(vinyl alcohol) hydrogel: preparation and assessment of thrombogenicity," Biomaterials (1992) 13(7):421-424.

Llanos, G.R. et al., "Immobilization of poly(ethylene glycol) onto a poly(vinyl alcohol) hydrogel: 2. Evaluation of thrombogenicity," J. Biomed. Res. (1993) 27:1383-1391.

Mehvar, R., "Modulation of the pharmacokinetics and pharmacodynamics of proteins by polyethylene glycol conjugation," J. Pharm. Pharm. Sci. (2000) 3:125-136.

Morpurgo et al., "Covalent modification of mushroom tyrosinase with different amphibic polymers for pharmaceutical and biocatalysis applications," App. Biochem. Biotech. (1996) 56:59-72.

Nagasaki et al., "Synthesis of heterotelechelic poly(ethylene glycol) macromonomers. Preparation of poly(ethylene glycol) possessing a methacryloyl group at one end and a formyl group at the other end," Macromolecules (1997) 30:6489-6493.

Nakamura et al., "Synthesis of heterobifunctional poly(ethylene glycol) with a reducing monosaccharide residue at one end," Bioconjugate Chem. (1998) 9:300-303.

Offner et al., "Chemical and swelling evaluations of amino group crosslinking in gelatin and modified gelatin matrices," Pharm. Res. (1996) 13:1821-1827.

Yokoyama et al., "Synthesis of poly(ethylene oxide) with heterobifunctional reactive groups at its terminals by an anionic initiator," Bioconjugate Chem. (1992) 3:275-276.

Zalipsky, S., "Functionalized poly(ethylene glycol) for preparation of biologically relevant conjugates," Bioconjugate Chem. (1995) 6:150-165.

Zalipsky et al., "Facile synthesis of α-hydroxy-ωcarboxymethylpolyethylene oxide," J. Bioact. Biocompatible Polym. (1990) 5:227-231.

Burmania, J. A. et al., "Cell interaction with protein-loaded interpenetrating networks containing modified gelatin and poly(ethylene glycol) diacrylate", Biomaterials, 24 (2003), pp. 3921-3930.

Burmania, J. A. et al., "Synthesis and physicochemical analysis of interpenetrating networks containing modified gelatin and poly(ethylene glycol) diacrylate", (2003), J Blomed Mater Res 67A: pp. 224-234, Wiley Periodicals, Inc.

Examination Report for European Pat. Appln. No. 02728891.9, dated Feb. 28, 2006, 5 pp.

Harris, J. M., "Laboratory Synthesis of Polyethylene Glycol Derivatives", Macromol. Chem. Phys., (1985) C25, pp. 325-373.

Hwang, D. C. et al., "Chemical Modification Strategies for Synthesis of Protein-Based Hydrogel," J. Agric. Food Chem., (1996), 44, pp. 751-758.

International Search Report for Intl. Appln. No. PCT/US2002/012621, dated Jul. 2, 2003, 1 p.

Methoden der Organischen Chemie, Houben-Weyl, Jrsg. Eu. Muller, Thieme Verlag, Stuttgart , (1970), Band XIII/1, p. 377.

Supplementary European Search Report for European Pat. Appln. No. 02728891.9, dated Oct. 5, 2005, 3 pp.

The Chemistry of Acrylonitrile, 2nd Edition, (1959), p. 17, The American Cyanamid Company, New York, NY.

The Merck Index, 12th Ed., (1996), No. 4388, pp. 742-743, Merck Research Laboratories, Division of Merck & Co., Inc.

Zalipsky et al., "Introduction to Chemical and Biological Applications of Poly(ethylene glycol)", American Chemical Society Polymer Preprints, (1997), 30:356, pp. 1-13.

Foreign Office Action for EPO Pat. Appln. No. 02728891.9, dated Jun. 6, 2011, 7 pp.

Kao et al.; Canadian Patent Office Action dated Jul. 16, 2007 for Application No. 2444880 filed Apr. 23, 2002 for Bifunctional-Modified Hydrogels; (3 pages).

Kao et al.; Canadian Patent Office Action dated Apr. 29, 2008 for Application No. 2444880 filed Apr. 23, 2002 for Bifunctional-Modified Hydrogels; (2 pages).

Kao et al.; European Patent Office Action dated Feb. 16, 2007 for Application No. 02728891.9 filed Apr. 23, 2002 for Bifunctional-Modified Hydrogels; (8 pages).

Kao et al.; European Patent Office Action dated Nov. 28, 2007 for Application No. 02728891.9 filed Apr. 23, 2002 for Bifunctional-Modified Hydrogels; (5 pages).

Kao et al.; European Patent Office Examination Report dated Nov. 21, 2008 for Application No. 02728891.9 filed Apr. 23, 2002 for Bifunctional-Modified Hydrogels; (6 pages).

Kao et al.; European Patent Office Examination Report dated Dec. 15, 2009 for Application No. 02728891.9 filed Apr. 23, 2002 for Bifunctional-Modified Hydrogels; (4 pages).

Kao et al.; Japanese Patent Office Action dated Aug. 8, 2006 (with English translation) for Application No. 2002-582992 filed Apr. 23, 2002 for Bifunctional-Modified Hydrogels; (13 pages).

Kao et al.; Japanese Patent Office Action dated Jan. 15, 2008 (with English translation) for Application No. 2002-582992 filed Apr. 23, 2002 for Bifunctional-Modified Hydrogels; (6 pages).

Kao et al.; United States Office Action dated Feb. 16, 2005 for U.S. Appl. No. 10/128,198, filed Apr. 23, 2002 for Bifunctional-Modified Hydrogels; (20 pages).

Kao et al.; United States Office Action dated Aug. 11, 2005 for U.S. Appl. No. 10/128,198, filed Apr. 23, 2002 for Bifunctional-Modified Hydrogels; (12 pages).

Kao et al.; United States Office Action dated Dec. 6, 2006 for U.S. Appl. No. 10/128,198, filed Apr. 23, 2002 for Bifunctional-Modified Hydrogels; (10 pages).

Kao et al.; United States Office Action dated Mar. 18, 2008 for U.S. Appl. No. 10/128,198, filed Apr. 23, 2002 for Bifunctional-Modified Hydrogels; (8 pages).

Kao et al.; United States Office Action dated May 8, 2007 for U.S. Appl. No. 10/128,198, filed Apr. 23, 2002 for Bifunctional-Modified Hydrogels; (11 pages).
Kao et al.; United States Office Action dated Oct. 7, 2008 for U.S. Appl. No. 10/128,198, filed Apr. 23, 2002 for Bifunctional-Modified Hydrogels; (9 pages).
Kao et al.; United States Office Action dated Jul. 24, 2009 for U.S. Appl. No. 11/093,531, filed Mar. 30, 2005 for Bifunctional-Modified Hydrogels; (8 pages).

Kao et al.; United States Office Action dated Mar. 8, 2007 for U.S. Appl. No. 11/273,393, filed Nov. 14, 2005 for Bifunctional-Modified Hydrogels; (18 pages).
Kao et al.; International Preliminary Examination Report dated Aug. 4, 2003 for Application No. PCT/US2002/012621 filed Apr. 23, 2002 for Bifunctional-Modified Hydrogels; (4 pages).

* cited by examiner

BIFUNCTIONAL-MODIFIED HYDROGELS

CROSS-REFERENCE TO RELATED APPLICATIONS

This patent application is a continuation of U.S. application Ser. No. 10/128,198 filed Apr. 23, 2002, now U.S. Pat. No. 7,615,593, which claims the benefit of priority to U.S. Provisional Application No. 60/285,782 filed Apr. 23, 2001. These applications are incorporated herein by reference in their entireties.

STATEMENT REGARDING FEDERALLY SPONSORED RESEARCH AND DEVELOPMENT

This invention was made with United States government support awarded by the following agencies: NIH HL63686. The United States government has certain rights in this invention.

FIELD OF THE INVENTION

The invention is directed to hydrogels modified using bifunctional reagents, use of the hydrogels to deliver drugs or other biologically-active agents to a mammal in need thereof, compositions containing the hydrogels described herein, and devices, such as wound dressings, diapers, catamenial devices, etc., incorporating the hydrogels.

INCORPORATION BY REFERENCE

All of the reference listed in the "References" section are incorporated herein.

BACKGROUND

Biological systems, such as healing and embryonic development, operate under spatially- and temporally-controlled orchestration. A myriad of signals and cells all act, in space and time, to heal a cut, for example, or to surround and neutralize a foreign body. The efficacy of current materials used to construct biomedical devices is limited by a lack of multi-functional structures to complement the inherent dynamics of these biological systems.

For example, most wound dressings provide nothing more than a simple barrier to shield the wound and to prevent foreign objects from entering the would. Other newer types of dressings also include antibiotics to prevent sepsis at the wound site. However, these dressings do not address, for example, the exudation which occurs from a wound. Thus, these dressings must be changed often.

Certain biodegradable polymers have been used in burn dressings, hemostatic patches, and the like. These biodegradable polymers provide a barrier and possibly a tissue scaffold for regrowth. However, these types of dressing have no therapeutic effect. While such types of dressings provide effective barriers to physical disturbance of the wound site, scarring is still extensive.

Despite the extensive investigation of novel wound dressing materials, very few materials are in current clinical use. An ideal functional wound dressing should have the following properties: It should be non-toxic, biocompatible, and permeable to moisture and gases to absorb wound exudate and toxins as well as maintain appropriate humidity and oxygen levels. It should be porous to prevent swelling of the wound bed and accumulation of the fluid between the wound site and the material. It should be flexible and durable and minimize local inflammation and infection, thereby promoting new vascularization, re-epithelialization, and normal healing.

Hydrogels are three-dimensional networks capable of absorbing copious amounts of water. Hydrogels have been explored for many uses, including drug delivery devices, wound dressing materials, contact lenses, and cell transplantation matrices. Edible hydrogels, such as gelatin, find extensive use in various food-related applications, such as texture modification, gelling, clarification of beers and wines, and as medicine capsules.

SUMMARY OF THE INVENTION

The invention is directed to hydrogels comprising a polymer matrix, preferably gelatin or a synthetic polymer (preferably a biodegradable polymer, although the polymer may also be non-biodegradable), modified to contain bifunctional poly(alkylene glycols) covalently bonded to the polymer matrix. Heterobifunctional, poly-$C_1$-$C_6$-poly(alkylene glycol) molecules, preferably poly(ethylene glycol) molecules (hPEGs), each having an $\alpha$-terminus and an $\omega$-terminus, are bonded to the polymer backbone via covalent bonds involving either of the $\alpha$- or $\omega$-termini. One or more biofunctional agents (i.e., pharmacologically-active agents) are then bonded to the other of the $\alpha$- or $\omega$-termini (i.e., the free termini) of the hPEGs, thereby yielding a modified, pharmacologically active, homogenous, and covalently-assembled hydrogel. A schematic representation of the preferred embodiment of the invention is shown in FIG. 4.

Any pharmacologically-active agent, without limitation, can be incorporated into the hydrogel, including (by way of illustration and not limitation) vulnerary agents, hemostatic agents, antibiotics, antithelmintics, anti-fungal agents, hormones, anti-inflammatory agents, proteins, polypeptides, oligonucleotides, cytokines, enzymes, etc.

The hydrogels of the present invention find many uses, the preferred of which is as a functional wound dressing. In this preferred embodiment, the hydrogel contains as a pharmacologically-active agent a vulnerary agent covalently bonded to a biodegradable polymer matrix via a differentially-modified, $\alpha$- and $\omega$-substituted PEG linker.

The hydrogels of the present invention may also be incorporated into bandages, surgical and dental wound packing material, diapers and catamenial devices, and the like.

The novel hydrogel constructs described herein are not physical blends, which are common in the formulation of current biomedical hydrogels; hence, the chemical and physical properties of the subject hydrogels are homogenous and can be tailored to suit a particular clinical end-point requirement. Furthermore, the hydrogel constructs are mechanically stable because the components are covalently bonded. In addition, the hydrophilicity and flexibility of the porous hydrogel accommodate the absorption of wound exudate and assist the final removal of the material from the wound site (if necessary or desired). The nature of gelatin and the porosity of the construct further facilitate the exchange of gases and allow healing. Most importantly, the presence of hPEG-conjugated bioactive compounds and the loading of other pharmaceutical compounds within the matrix allows for the temporally- and spatially-controlled delivery of bioactive signals to modulate and complement the dynamics of the host healing process.

The present invention offers several key commercial advantages over existing products. For example, despite the extensive investigation in the development of novel wound dressing materials, very few materials are used clinically due to the multiple requirements necessary for a functional wound dressing. Ideal functional wound dressings must be nontoxic, biocompatible, permeable to moisture and gases to absorb wound exudate and toxins, as well as to maintain humidity and oxygen levels. The dressings should be porous to prevent swelling of the wound bed and to prevent accumulation of fluid between the wound site and the material. They should be flexible and durable. They should be biocompatible and minimize local inflammation and infection. They should promote neovascularization, re-epithelialization, and normal healing. The novel multi-functional hydrogels described herein can be made to address all of the above requirements for a clinically viable wound dressing material.

Thus in a first embodiment, the invention is directed to a hydrogel that comprises a polymer matrix. The preferred polymer matrix contains reactive amino groups. The most preferred polymer matrices are gelatin and collagen. The polymer matrix is modified using a bifunctional modifier comprising a poly(alkylene glycol) molecule having a substituted or unsubstituted α-terminus and a substituted or unsubstituted ω-terminus. At least one of the α- or ω-termini is covalently bonded to the polymer matrix. The other terminus projects into the interior of the hydrogel mass and modifies its physico-chemical properties. By controlling the nature of the α- and ω-termini, the physical and chemical qualities of the resulting hydrogel can be altered.

Additionally, in the preferred embodiment, the α- and ω-termini are different, and thus are differentially reactive. This enables, for example, one or more pharmacologically-active agents to be covalently bonded to one of the α- or ω-termini that is not bonded to the polymer matrix. Alternatively (or simultaneously), one or more pharmacologically-active agents may also be entrained within the hydrogel.

The polymer matrix of the hydrogel may be cross-linked with a cross-linking reagent such as glutaraldehyde. Cross-linking alters the absorption characteristics and material strength of the resulting gel. Thus, cross-linking may be desirable where increased mechanical strength of the gel is required.

As noted above, the α- and/or ω-termini of the hydrogel may be substituted or unsubstituted. When substituted, it is preferred that the substitution is a moiety selected from the group consisting of halo, hydroxy, $C_1$-$C_{24}$-alkenyl, $C_1$-$C_{24}$-alkynyl, $C_1$-$C_{24}$-alkoxy, $C_1$-$C_{24}$-heteroalkyl, $C_1$-$C_{24}$-heteroalkenyl, $C_1$-$C_{24}$-heteroalkynyl, cyano-$C_1$-$C_{24}$-alkyl, $C_3$-$C_{10}$-cycloalkyl, $C_3$-$C_{10}$-cycloalkenyl, $C_3$-$C_{10}$-cycloalkynyl, $C_3$-$C_{10}$-cycloheteroalkyl, $C_3$-$C_{10}$-cycloheteroalkenyl, $C_3$-$C_{10}$-cycloheteroalkynyl, acyl, acyl-$C_1$-$C_{24}$-alkyl, acyl-$C_1$-$C_{24}$-alkenyl, acyl-$C_1$-$C_{24}$-alkynyl, carboxy, $C_1$-$C_{24}$-alkylcarboxy, $C_1$-$C_{24}$-alkenylcarboxy, $C_1$-$C_{24}$-alkynylcarboxy, carboxy-$C_1$-$C_{24}$-alkyl, carboxy-$C_1$-$C_{24}$-alkenyl, carboxy-$C_1$-$C_{24}$-alkynyl, aryl, aryl-$C_1$-$C_{24}$-alkyl, aryl-$C_1$-$C_{24}$-alkenyl, aryl-$C_1$-$C_{24}$-alkynyl, heteroaryl, heteroaryl-$C_1$-$C_{24}$-alkyl, heteroaryl-$C_1$-$C_{24}$-alkenyl, heteroaryl-$C_1$-$C_{24}$-alkynyl, sulfonate, arylsulfonate, and heteroarylsulfonate.

Moreover, these moieties themselves may be further substituted. Thus, the moieties on the α-terminus and the ω-terminus when substituted bear a substituent selected from the group consisting of alkyl, aryl, acyl, halogen, hydroxy, amino, alkoxy, alkylamino, acylamino, thioamido, acyloxy, aryloxy, aryloxyalkyl, mercapto, thia, aza, oxo, saturated cyclic hydrocarbon, unsaturated cyclic hydrocarbon, heterocycle, aryl, and heteroaryl.

More specifically, the invention is directed to a hydrogel comprising:
a polymer matrix containing reactive amino acid moieties; and
a bifunctional modifier comprising a compound of formula:

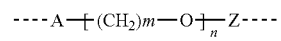

wherein at least one of the "A" or "Z" moieties is covalently bonded to the reactive amino moieties of the polymer matrix; and wherein "A" and "Z" are independently selected from the group consisting of hydrogen, halo, hydroxy, $C_1$-$C_{24}$-alkyl, $C_1$-$C_{24}$-alkenyl, $C_1$-$C_{24}$-alkynyl, $C_1$-$C_{24}$-alkoxy, $C_1$-$C_{24}$-heteroalkyl, $C_1$-$C_{24}$-heteroalkenyl, $C_1$-$C_2$-heteroalkynyl, cyano-$C_1$-$C_{24}$-alkyl, $C_3$-$C_{10}$-cycloalkyl, $C_3$-$C_{10}$-cycloalkenyl, $C_3$-$C_{10}$-cycloalkynyl, $C_3$-$C_{10}$-cycloheteroalkyl, $C_3$-$C_{10}$-cycloheteroalkenyl, $C_3$-$C_{10}$-cycloheteroalkynyl, acyl, acyl-$C_1$-$C_{24}$-alkyl, acyl-$C_1$-$C_{24}$-alkenyl, acyl-$C_1$-$C_{24}$-alkynyl, carboxy, $C_1$-$C_{24}$-alkylcarboxy, $C_1$-$C_{24}$-alkenylcarboxy, $C_1$-$C_{24}$-alkynylcarboxy, carboxy-$C_1$-$C_{24}$-alkyl, carboxy-$C_1$-$C_{24}$-alkenyl, carboxy-$C_1$-$C_{24}$-alkynyl, aryl, aryl-$C_1$-$C_{24}$-alkyl, aryl-$C_1$-$C_{24}$-alkenyl, aryl-$C_1$-$C_{24}$-alkynyl, heteroaryl, heteroaryl-$C_1$-$C_{24}$-alkyl, heteroaryl-$C_1$-$C_{24}$-alkenyl, heteroaryl-$C_1$-$C_{24}$-alkynyl, sulfonate, arylsulfonate, and heteroarylsulfonate; "m" is an integer of from 2 to 8; and "n" is an integer equal to or greater than 100. In the preferred embodiment, "m" equals 2 and "n" is greater than 2,000.

A second embodiment of the invention is directed to a hydrogel as described above, with the further inclusion of a second polymer matrix. In this embodiment, the second polymer matrix interpenetrates with the first polymer matrix. Thus, the first polymer matrix, with its grafted modifier molecules, interpenetrates and is physically bound within a second, interpenetrating polymer matrix. In the preferred second embodiment, the second polymer matrix comprises a photopolymerized poly(acrylate), such as an α-acrylate-ω-acrylate-poly(alkylene glycol), trimethylolpropane triacrylate, acrylic acid, and/or acryloyl halide. The second polymer matrix may be a homo-polymer or co-polymer or two or more monomer types.

As in the first embodiment, the interpenetrating hydrogels may further comprise a pharmacologically-active agent covalently bonded to one of the α- or ω-termini that is not bonded to the first polymer matrix.

Likewise, all of the hydrogels according to the present invention may further comprise a pharmacologically-active agent or a living cell entrained within the hydrogel.

A third embodiment of the invention is directed to a method of making a hydrogel as described hereinabove. The method comprises reacting a polymer matrix with a bifunctional modifier comprising a poly(allylene glycol) molecule having a substituted or unsubstituted α-terminus and a substituted or unsubstituted ω-terminus, whereby at least one of the α- or ω-termini is covalently bonded to the polymer matrix.

A fourth embodiment of the invention is directed to the method described in the previous paragraph, and further comprising contacting the first polymer matrix with a plurality of monomers and then polymerizing the monomers to yield a second polymer matrix, wherein the second polymer matrix interpenetrates with the first polymer matrix. This embodiment allows for the in situ formation of interpenetrating polymer networks The hydrogels of the present invention can be used in any application where hydrogels are currently employed. Thus, the hydrogels of the present invention find use as wound dressings, diapers, catamenial devices, and the like. In one embodiment, the hydrogels are used to administer a pharmacologically-active agent to a patient in need of the pharmacologically-active agent. In this use, the pharmacologically-active agent either is covalently bonded within the gel or entrained within the gel. The gel is then administered to the patient, as by packing it into a surgical or traumatic wound.

The hydrogels of the present invention are also useful as scaffolds to support living cells. Thus, the hydrogels of the present invention can be used as biomechanical devices. The hydrogels will support living cells within the bulk of the gel, thereby providing a three-dimensional support network in which the cells can grow and proliferate. Hydrogels according to the present invention that contain cells can be implanted into a patient in need of such cells.

DETAILED DESCRIPTION OF THE INVENTION

Figure 1:
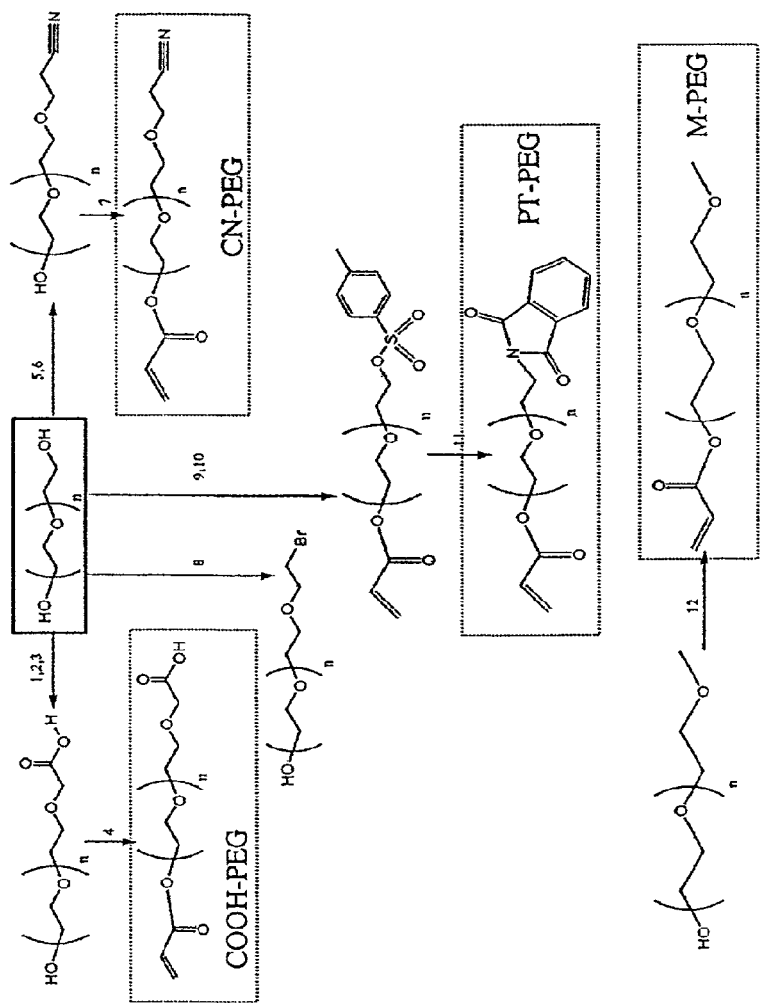
FIG. 1. A summary of the chemical reactions and structure of critical intermediates and final products of M-PEG, CN-PEG, COOH-PEG, or PT-PEG. (1) sodium/naphthalene, THF, room temperature; (2) ethyl bromoacetate, TEA, THF, room temperature; (3) sodium hydroxide solution, reflux; (4) AC, TEA, THF, 10 min room temperature; (5) sodium ethoxide (or sodium metal), $CH_2Cl_2$, room temperature; (6) acrylonitrile room temperature; (7) AC, TEA, THF, 10 min room temperature; (8) TEA, thionyl bromide, toluene, reflux; (9) p-toluenesulfonylchloride, TEA, $CH_2Cl_2$, room temperature; (10) AC, TEA, THF, 10 min room temperature; (11) potassium phthalimide, $CH_2Cl_2$, reflux; (12) AC, TEA, THF, 10 min room temperature FIGS. 2A and 2B. HPLC chromatogram of (2A) evaporative light scattering detector signals and (2B) UV signals at 254 nm for PEGdiols and various XPEGmA. Samples were analyzed with a reverse phase HPLC system (10% to 100% acetonitrile at a flow rate of 1 ml/min in 30 min with Jordi 500 A column on a Gilson system) coupled to UV/Vis (200 nm and 254 nm), photodiode array, and evaporative light scattering detectors.

Poly(alkylene glycols), such as poly(ethylene glycol) (PEG), are employed extensively in a number of medical and pharmaceutical fields due to their low toxicity, good biocompatibility, and excellent solubility[1-5]. For sake of expository brevity, the following description shall be limited to gels modified by bifunctional poly(ethylene glycol) molecules. The invention, however, will function with equal success using any poly(alkylene glycol).

Thus, it is preferred that the bifunctional modifier comprise a poly(alkylene glycol) of the formula:

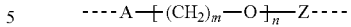

where "m" is an integer of from 2 to 8; "n" is an integer equal to or greater than 100; and "A" and "Z" are as described above. In the preferred embodiment, "m" equals 2 and "n" is sufficiently large to yield a PEG molecule having a molecular weight of roughly 100,000 Da. Thus, it is preferred that "n" is greater than 2,000. The "n" substituent may also be sufficiently large to yield a PEG molecule having a molecular weight greater than $1 \times 10^6$ Da, in which case "n" is greater than roughly 20,000.

While having good biocompatibility and solubility, the hydroxyl groups in PEG-diols or monomethoxy-PEGs have very limited chemical activity. The present invention thus is drawn to novel hydrogels that use bifunctional PEGs and hetero-bifunctional PEGs ("hPEGs") as covalent grafts to modify the physical and biological properties of hydrogels. These bifunctional PEGS having improved reactivity and physicochemical properties can thus be used to modify polymer matrices in general, and proteinaceous matrices in particular, to yield novel hydrogels. These novel hydrogels are useful in wide array of biomaterial and biopharmaceutical compositions and devices that include a hydrogel component, including time-release vehicles, wound dressings and packing, bandages, burn dressings, catamenial devices, diapers, etc.

Currently, the synthesis of hPEGs is classified into two general categories: 1) statistical terminal modification of PEG precursors; and 2) ethylene oxide polymerization methods using special initiators.[6-9] Although various hPEGs are currently available commercially (e.g., from Shearwater Corporation, Huntsville, Ala.), their high cost and limited quantity greatly restricts the extensive utilization of such materials by laboratories in developing novel biomaterials for various applications. In developing the present invention, a number of synthetic schemes were developed to produce a library of hPEG compounds based on the statistical terminal modification method.

A distinct benefit of the various reaction schemes is that they use as a starting material commercially-available PEG-diols. PEG-diol is available in a host of different molecular weights, and from a large number of international suppliers (including Shearwater Corporation).

Moreover, the synthetic strategy is streamlined so modifications to various intermediates results in the formulation of different hPEG products.

Using the hPEGs of the present invention, polymer networks having diverse physicochemical and surface properties were developed. These networks can be used to study cell-material interaction.[10-13]

In the Examples that follow, hPEGs were utilized to modify a polymer matrix to yield novel hydrogels. The effect of hPEG concentration, molecular weight, and terminal chemical functionality on the surface hydrophobicity and cell interaction with the hydrogels was investigated and is presented in the Examples. Multiple heterogeneous PEG modifications (e.g., carboxylic acids of the poly-acrylic acid backbone and the functional group at the dangling terminus of hPEG grafted at the pendent chain configuration) can be employed to bind several distinct types of biofunctional molecules such as peptides and pharmaceutics to the hydrogel.

These components therefore are highly useful as functional wound dressings. In the preferred embodiment, the polymer matrix is a modified gelatin. The use of gelatin is not incidental. Gelatin is a well-characterized, FDA approved, biodegradable biomaterial. Thus, hydrogels made from modified gelatin are likely to pass regulatory muster due to the known safety of gelatin.

The hydrophilicity and porosity of gelatin was modified using ampholytic moieties such as ethylenediaminetetracetic dianhydride (EDTAD). The resulting polymer backbone can be cross-linked with small amounts of glutaraldehyde and subsequently loaded with pharmaceutical agents such as antibiotic drugs. The water-uptake, swelling, degradation, and drug release kinetics of the resulting hydrogel can be controlled by varying the amount of cross-linking and the extent of EDTAD modification.

To improve its biocompatibility and mechanical properties, the hydrogel was then grafted with various hPEGs, as described hereinbelow.

To investigate the functional properties of these novel biomaterials, the interaction of hPEGs, hPEG-modified gelatin hydrogels, and synthetic polymer networks containing human white blood cells and fibroblasts were examined, both in vitro and in vivo. The terminal group of the hPEGs has also been used to link bioactive peptides to the hydrogel matrix, thereby to control the interaction of host cells such as white blood cells and to enhance favorable biological interactions. It has been demonstrated in the Examples that the molecular interaction of several bioactive oligopeptides in modulating white blood cell behavior and host interaction in vitro and in vivo can thus be modified.

The resulting hydrogels can be used a functional wound dressings, bandages, and the like. These functional wound dressings are suitable for use both internally and externally. The gelatin-hPEG hydrogels of the present invention have been tested in a subcutaneous caged implant model.

One notable aspect of the hydrogels of the present invention is that the polymer constructs are not physical blends. The present hydrogels are chemically and physically homogenous and can be tailored to suit a particular clinical endpoint requirement. The hydrogel is mechanically stable because the components are covalently bonded together. Additionally, the hydrophilicity and flexibility of the porous hydrogel accommodates the absorption of wound exudate, blood, etc., and assists in the final removal of material from the wound site.

The nature of gelatin and the porosity of the construct also facilitates the exchange of gases and promotes rapid healing. Most importantly, the presence of hPEG-conjugated bioactive compounds within the hydrogel matrix itself adds qualitative value and control to the wound healing process.

As described hereinbelow, a synthetic scheme was developed to created a library of heterobifunctional PEGs (hPEGs) having two distinct terminal moieties. The hPEGs were then used to make modified polymer hydrogels having various surface and physicochemical properties. Extensive NMR and HPLC analyses confirmed the chemical structure of hPEG. The hydrophilicity of the polymer network was predominantly dependent on the hPEG concentration, with the molecular weight of the starting, unmodified PEG and the terminal functional groups also playing roles. Adherent human fibroblast density on the hydrogels remained constant with increasing hPEG concentration in the gel formulation but decreased rapidly on hydrogels containing 0.8 to 1.25 g/ml of hPEGs. This trend was independent of the hPEG terminal moiety and molecular weight. No adherent cells were observed on all sample gels containing 2.5 g/ml or more of hPEGs.

Abbreviations and Definitions:

"Ac" = acrylic acid
"AC" = acryloyl chloride (CAS No. 814-68-6)
"CHD" = chlorhexidine digluconate
"CN-PEG" = α-cyanoethyl-ω-acrylate-PEG
"COOH-PEG" = α-carboxyl-ω-acrylate-PEG
"EDTAD" = ethylene diaminetetracetic dianhydride
"hPEG" = heterobifunctional PEG
"IPN" = interpenetrating network hydrogels
"mPmA" = α-methyl-ω-aldehyde-PEG
"mPEG" = α-methoxy-PEG
"M-PEG" = α-methyl-ω-acrylate-PEG
"PEG" and "PEG diol" = polyethylene glycol
"PEGdA" = PEG-diacrylate
"PEG dial" = α-aldehyde-ω-aldehyde-PEG
"PT-PEG" = α-phthalimide-ω-acrylate-PEG
"TEA" = triethylamine
"THF" = tetrahydrofuran
"TMPTA" = trimethylolpropane triacrylate (i.e., 2-ethyl-2-(hydroxymethyl)-1,3-propanediol triacrylate, CAS No. 15625-89-5)
"XPEGmA" = hPEG with acrylate ω-terminal and α-terminal of different moiety The term "alkyl," by itself or as part of another substituent, means, unless otherwise stated, a fully saturated, straight, branched chain, or cyclic hydrocarbon radical, or combination thereof, and can include di- and multi-valent radicals, having the number of carbon atoms designated (e.g., $C_1$-$C_{10}$ means from one to ten carbon atoms, inclusive). Examples of alkyl groups include, without limitation, methyl, ethyl, n-propyl, isopropyl, n-butyl, t-butyl, isobutyl, sec-butyl, cyclohexyl, (cyclohexyl)ethyl, cyclopropylmethyl, and homologs and isomers thereof, for example, n-pentyl, n-hexyl, n-heptyl, n-octyl, and the like. The term "alkyl," unless otherwise noted, also includes those derivatives of alkyl defined in more detail below as "heteroalkyl" and "cycloalkyl."

The term "alkenyl" means an alkyl group as defined above containing one or more double bonds. Examples of alkenyl groups include vinyl, 2-propenyl, crotyl, 2-isopentenyl, 2-(butadienyl), 2,4-pentadienyl, 3-(1,4-pentadienyl), etc., and the higher homologs and isomers.

The term "alkynyl" means an alkyl or alkenyl group as defined above containing one or more triple bonds. Examples of alkynyl groups include ethynyl, 1- and 3-propynyl, 3-butynyl, and the like, including the higher homologs and isomers.

The terms "alkylene," "alkenylene," and "alkynylene," alone or as part of another substituent means a divalent radical derived from an alkyl, alkenyl, or alkynyl group, respectively, as exemplified by —$CH_2CH_2CH_2CH_2$—.

Typically, alkyl, alkenyl, alkynyl, alkylene, alkenylene, and alkynylene groups will have from 1 to 24 carbon atoms. Those groups having 10 or fewer carbon atoms are preferred in the present invention. The term "lower" when applied to any of these groups, as in "lower alkyl" or "lower alkylene," designates a group having eight or fewer carbon atoms.

"Substituted" refers to a chemical group as described herein that further includes one or more substituents, such as lower alkyl, aryl, acyl, halogen (e.g., alkylhalo such as $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl, alkenyl, alkynyl, alkylene, alkenylene, and alkynylene moieties. Additionally, these groups may be pendent from, or integral to, the carbon chain itself.

The term "heteroalkyl," by itself or in combination with another term, means, unless otherwise stated, a stable, saturated or unsaturated, straight, branched chain, or cyclic hydrocarbon radical, or combinations thereof, consisting of the stated number of carbon atoms and from one to three heteroatoms selected from the group consisting of O, N, Si, and S, and wherein the nitrogen and sulfur atoms may optionally be oxidized and the nitrogen heteroatom(s) may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as in —CH$_2$—NH—O—CH$_3$ and —CH$_2$—O—Si(CH$_2$)$_3$. Explicitly included within the term "heteroalkyl" are those radicals that could also be described as "heteroalkylene" (i.e., a divalent radical, see next paragraph), and "heterocycloalkyl" (i.e., containing a cyclic group). The term "heteroalkyl" also explicitly includes unsaturated groups (i.e., heteroalkenyls and heteroalkynyls).

The term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$—NH—CH$_2$—. For heteroalkylene groups, heteroatoms can also occupy either or both of the chain termini. Still further, for alkylene and heteroalkylene linking groups, no orientation of the linking group is implied.

The term "aryl" is used herein to refer to an aromatic substituent, which may be a single aromatic ring or multiple aromatic rings which are fused together, linked covalently, or linked to a common group such as a diazo, methylene or ethylene moiety. The common linking group may also be a carbonyl as in benzophenone. The aromatic ring(s) may include, for example phenyl, naphthyl, biphenyl, diphenylmethyl and benzophenone, among others. The term "aryl" encompasses "arylalkyl" and "substituted aryl." For phenyl groups, the aryl ring may be mono-, di-, tri-, tetra-, or penta-substituted. Larger rings may be unsubstituted or bear one or more substituents.

"Substituted aryl" refers to aryl as just described including one or more functional groups such as lower alkyl, acyl, halogen, alkylhalo (e.g., CF$_3$), hydroxy, amino, alkoxy, alkylamino, acylamino, acyloxy, phenoxy, mercapto, and both saturated and unsaturated cyclic hydrocarbons which are fused to the aromatic ring(s), linked covalently or linked to a common group such as a diazo, methylene, or ethylene moiety. The linking group may also be a carbonyl such as in cyclohexyl phenyl ketone. The term "substituted aryl" encompasses "substituted arylalkyl."

The term "acyl" is used to describe a ketone substituent, —C(O)R, where R is substituted or unsubstituted alkyl, alkenyl, alkynyl, or aryl as defined herein. The term "carbonyl" is used to describe an aldehyde substituent. The term "carboxy" refers to an ester substituent or carboxylic acid, i.e., —C(O)O— or —C(O)—OH.

The term "halogen" or "halo" is used herein to refer to fluorine, bromine, chlorine and iodine atoms.

The term "hydroxy" is used herein to refer to the group —OH.

The term "amino" is used to designate NRR', wherein R and R' are independently H, alkyl, alkenyl, alkynyl, aryl or substituted analogs thereof. "Amino" encompasses "alkylamino," denoting secondary and tertiary amines, and "acylamino" describing the group RC(O)NR'.

The term "alkoxy" is used herein to refer to the —OR group, where R is alkyl, alkenyl, or alkynyl, or a substituted analog thereof. Suitable alkoxy radicals include, for example, methoxy, ethoxy, t-butoxy, etc. The term "alkoxyalkyl" refers to ether substituents, monovalent or divalent, e.g. —CH$_2$—O—CH$_3$ and —CH$_2$—O—CH$_2$—.

The term "gelatin" as used herein means any and all kinds of gelatin, of any type (e.g., Type A from pork, with an isoelectric point between about 7.0 and 9.0, and Type B from beef with an isoelectric point of approximately 5.0), from any source, of any bloom value, acid- or alkaline-treated, etc., without limitation. The "bloom strength" of a gelatin is defined as the force required for a plunger of defined shape and size to make a 4 mm depression in a gel that has been prepared at 6.67% w/w concentration and chilled at 10° C. in a bloom jar for 16-18 hours. The force is recorded in grams. Commercially, gelatin is available from a host of commercial suppliers. At commodity amounts and prices, gelatin is generally available with bloom strengths ranging from about 50-300 bloom. Such gelatins are available from, for example, Leiner Davis Gelatin, a wholly-owned subsidiary of Goodman Fielder Ingredients of Sydney, Australia. Gelatins having bloom values outside this range are also available as specialty chemicals and are included within the scope of the term "gelatin." For example a zero bloom (non-gelling) gelatin is available from Great Lakes Gelatin Co., Grayslake, Ill.

Likewise, the term "collagen" as used herein means any and all kinds of collagen, of any type, from any source, without limitation. Cross-linked collagen, esterified collagen, and chemically-modified collagen, such as that taught by U.S. Pat. No. 4,390,519, are included with the term "collagen."

The term "polymer matrix" encompasses any type of polymer matrix that can function as a hydrogel, including, without limitation, gelatin, calcium alginate, calcium/sodium alginate, collagen, oxidized regenerated cellulose, carboxymethylcellulose, amino-modified celluloses, such as 6-deoxy-6-(4-aminophenyl)-amino-2(3)-O-tosylcellulose, whey protein gels, and the like.

The term "photopolymerizable acrylate" refers to any acrylate-containing molecule capable of being photopolymerized, without limitation. Expressly included within this definition are bis-diacrylate-PEGs, i.e., poly(alkylene glycol) molecules having an α-acrylate moiety and an ω-acrylate moiety. TMPTA is also a photopolymerizable acrylate.

Modified PEGs:

Commercial PEG-diols can be purchased essentially as a commodity item, in large amounts and at relatively inexpensive prices. The first step in modifying the α- and ω-termini of the PEG-diols is to convert them in aldehyde groups. This is very easily accomplished by treating the PEG-diol with acetic anhydride:

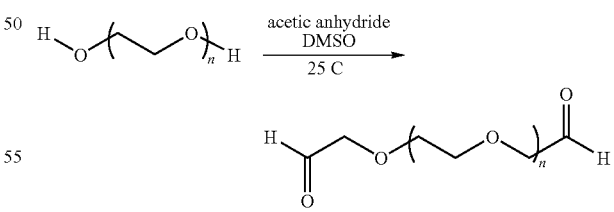

The reaction is very facile and quantitative.

With the PEG-dialdehyde in hand, the molecule can be further modified using any of the routes shown in FIG. 1, among many others. For example, as shown in FIG. 1, the PEG-diol can be converted into an α-hydroxy-ω-carboxy-PEG, which can then be converted into an α-acrylate-ω-carboxy-PEG. Or the PEG-diol can be converted into a α-hydroxy-ω-cyanoethyl-PEG, which can then, in turn, be converted into a α-acrylate-ω-cyanoethyl-PEG.

The PEG-diol can be directly converted, by simple halogenation of the hydroxy group to α-hydroxy-ω-halo-PEG. The PEG diol can also be tosylated and acrylated to thereby yield α-acrylate-ω-tosylated-PEG. The tosyl group can be exchanged for a succinimidyl or phthalimidyl or other nitrogen-containing heterocycle group. α-Hydroxy-ω-methoxy-PEG can be converted directly into α-acrylate-ω-methoxy-PEG. See FIG. 1. (See also Hern & Hubbell, (1998) *J. Biomed. Mater. Res.* 39:266-276; Morpurgo et al. (1996) *App. Biochem. Biotech.* 56:59-72; and Abuchowski et al. (1984) *Cancer Biochem. Biophys.* 7:175-186.)

Thus, for example, α-hydroxy-ω-glutarate-PEG can be synthesized by treating a PEG-diol with glutaric anhydride and glutaric acid in THF with gentle heating:

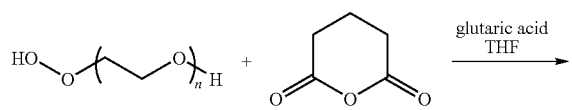

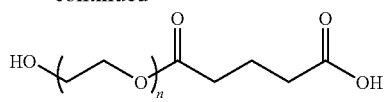

The glutaric anhydride and the glutaric acid are added and the solution gently heated to 55° C. The solution is maintained at that temperature, with stirring, for one day. The solution is then cooled to room temperature and filtered. The filtrate is then precipitated in cold hexane, the resulting precipitate is then removed by filtration, and dried in a vacuum to yield the desired product, generally a mixture of PEG-bis-glutarate and α-hydroxy-ω-glutarate-PEG. The two can be separated chromatographically (see the Examples).

The glutarate group can be further reacted to add a nitrogen-containing heterocycle, such as a succinimidyl group by reacting the α-hydroxy-ω-glutarate-PEG with N-hydroxy-succinimide in the presence of a water-soluble carbodiimide:

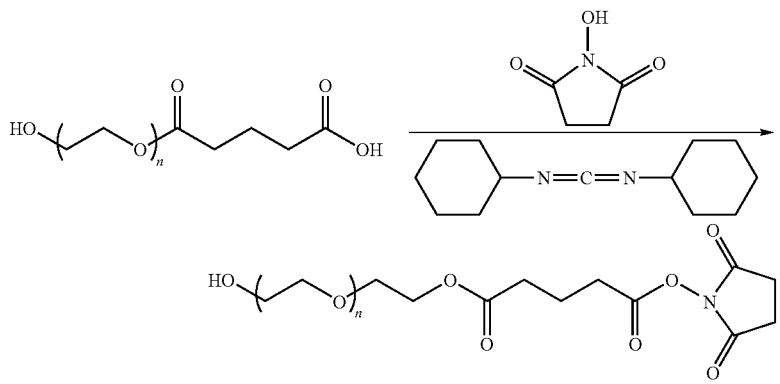

The N-hydroxy-succinimide is added and the solution cooled to 0° C. The dicyclohexylcarbodiimide (DCC) is added dropwise and the solution stirred for one day and filtered. The filtrate is precipitated by adding cold hexane. The resulting precipitate is filtered and dried in a vacuum. This yields the desired product, generally a mixture of PEG-bis-N-succinimidylglutarate and α-glutarate-ω-succinimidylglutarate-PEG (or α-hydroxy-ω-succinimidylglutarate-PEG, depending upon the starting material chosen). The two can be separated chromatographically (see the Examples).

The α-hydroxy-ω-succinimidylglutarate can be further reacted to yield α-acrylate-ω-succinimidylglutarates by reacting the α-hydroxy-ω-succinimidylglutarate with acrylic acid in the presence of TEA.

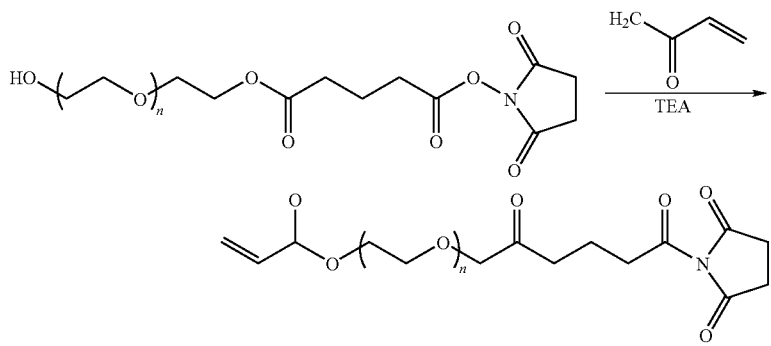

The PEG molecules may also be modified to introduce other amide bonds into the molecule. The formation of an amide bond is, of course, extremely useful in modifying the PEG molecule to contain an amino acid, peptide, or protein terminus. Thus, for example α-succinimidylglutarate-ω-tryptophanylglutarate PEG can be synthesized by dissolving the peptide or amino acid in 0.1 M 2-(N-morpholino)-ethanesulfonic acid (MES) at 0° C. α,ω-Bis-N-succinimidylglutarate-PEG is added dropwise to the solution with constant stirring. The reaction is allowed to continue at 0° C. for 1 hour and then allowed to come to room temperature with constant stirring for 4 hours. The reaction solution is then dialyzed against 50 volumes of deionized water and the resulting solution lyophilized. This yields the desired α-N-succinimidyl-glutarate-ω-tryptophanylglutarate in roughly 40% yield.

The modified PEGs can be attached to a polymer matrix containing amino-reactive groups using the same procedure as in the previous paragraph, thereby grafting the modified PEG to the amino-reactive groups of the polymer matrix. See also the Examples. In short, the mono- or dialdehyde-PEG is first dissolved in water. A separate aqueous solution of NaCNBH$_3$ is also prepared. The two solutions are then added simultaneously to a dilute (5%) solution of gelatin in water. The reaction is allowed to proceed overnight with gentle heating (50 to 60° C.). The modified gelatin is then separated by filtration.

Using these various synthetic schemes, the following modified PEG molecules have been made and used to modify gelatin to yield novel hydrogels that fall within the scope of the present invention:

Series 1: Alpha-Methoxy Heterobifunctional PEG Derivatives:

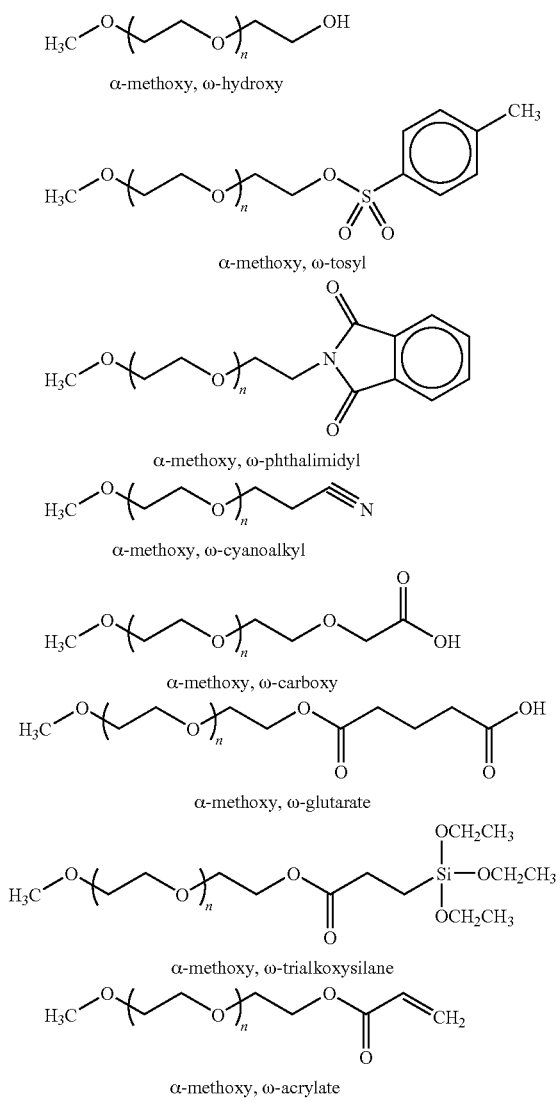

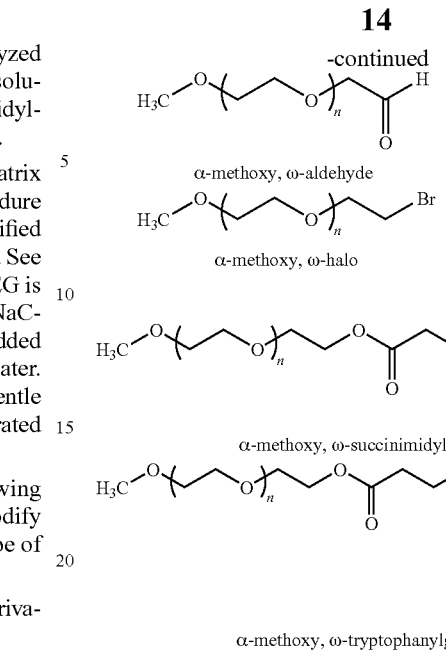

Series 1 Chemistry:

1.1. α-Methoxy, ω-hydroxy-PEG is commercially available (Shearwater).

1.2. To synthesize α-methoxy, ω-tosyl PEG, PEG (1 eq.) was dissolved in dry methylene chloride MC followed by addition of p-toluenesulfonylchloride (1 eq.) and triethylamine (1 eq.). The solution was stirred at room temperature for 48 hr, precipitated in cold hexane, collected by filtration and dried in vacuum oven for 24 hr.

1.3. To synthesize α-methoxy, ω-phthalimidyl PEG, α-methoxy, ω-tosyl PEG (1 eq.) from series 1-2 and potassium phthalimide (1.2 eq.) were dissolved in toluene and stirred at 50° C. for 20 hr. The solution was cooled down, filtered and the filtrate was precipitated in cold hexane, collected by filtration and dried in vacuum oven for 24 hr.

1.4. To synthesize α-methoxy, ω-cyanoalkyl PEGs, PEG (1 eq.) was dissolved in dry MC solution followed by the addition of fine sodium metal (1.5 eq.) and stirred for 12 hr at room temperature. Excess amount of acrylonitrile was added to the solution, stirred for 12 hr, filtered, and dried by rotary evaporation.

1.5. To synthesize α-methoxy, ω-carboxy PEG, PEG (1 mol) was dissolved in dry THF. Sodium (1.2 eq.) and naphthalene (1.2 eq.) were dissolved in dry THF and stirred under argon for 1 hr. The sodium/naphthalene solution was added dropwise to the PEG solution and the solution was stirred under argon for 4 hr. Ethyl bromoacetate (1.2 eq.) was then added and the solution was stirred under argon for 12 hr. The solution was filtered and the filtrate was precipitated in cold hexane, collected by filtration and dried in vacuum oven for 24 hr. The dried substance was dissolved in deionized water followed by addition of sodium hydroxide (1 eq.). The solution was stirred at 40° C. for two hr, extracted by MC or two times and evaporated by rotary evaporation.

1.6. To synthesize α-methoxy, ω-glutarate PEG, PEG (1 eq.) was dissolved in dry THF followed by addition of glutaric anhydride (1.5 eq.) and glutaric acid (0.001 eq.). The solution was stirred at 70° C. for 48 hr, cooled down, precipitated in cold hexane, collected by filtration and dried in vacuum oven for 24 hr.

1.7. To synthesize α-methoxy, ω-triethoxysilane PEG, α-methoxy, ω-acrylate PEG (1 eq.) from series 2-8 was dissolved in dry THF followed by addition of triehyoxysilane (5 eq.) and chloroplatinic acid (a grain). The solution was stirred at 60° C. for 48 hr, cooled down, precipitated in cold hexane, collected by filtration and dried in vacuum oven for 24 hr.

1.8. To synthesize α-methoxy, ω-acrylate PEG, PEG (1 eq.) was dissolved in dry THF followed by the addition of acryloyl chloride (2 eq.) and triethylamine (2.2 eq.). The solution was stirred at room temperature for 2 hr, filtered and the filtrate was precipitated in cold hexane, collected by filtration and dried in vacuum oven for 24 hr.

1.9. To synthesize α-methoxy, ω-aldehyde PEG, PEG (1 eq.) was dissolved in DMSO and the solution was added dropwise to the acetic anhydride (20 eq.) and stirred at room temperature for 2 hr. Ether was then added to the solution and stirred for 5 min at room temperature and placed in the −20° C. freezer for 5 minutes to precipitate. The precipitate was collected by filtration and then dissolved in minimal amounts of methylene chloride and reprecipitated likewise twice by ether. The precipitate was dried in vacuum oven for 24 hr.

1.10. To synthesize α-methoxy, ω-halo PEG, PEG (1 eq.) was dissolved in toluene followed by addition of triethylamine (1.2 eq.). The solution was stirred at 60° C. for 30 min followed by addition of thionyl bromide (1.2 eq.) and stirred at 60° C. for 1 hr. The hot solution was filtered through celite and the filtrate was kept in refrigerator at −4° C. for 24 hr. The precipitate was collected by filtration and dried in vacuum oven for 24 hr.

1.11. To synthesize α-methoxy, ω-succinimidylglutarate-PEG, α-methoxy, ω-glutarate PEG (1 eq.) from series 1.6 and dicyclohexylcarbodiimide (DCC 1.2 eq.) was dissolved in dry THF respectively. N-hydroxy succinimide (1.2 eq.) was added to the PEG solution followed by dropwise addition of DCC solution. The mixture solution was stirred at room temperature for 6 hr, filtered and the filtrate was precipitated in cold hexane, collected by filtration and dried in a vacuum oven for 3 days and then stored under argon at −4° C. in the refrigerator.

1.12. To synthesize α-methoxy, ω-succinimidylglutrate PEG, α-methoxy, ω-succinimidylglutrate PEG (1 eq.) from series 1.11 was dissolved in DMF followed by addition of tryptophan (1.5 eq.). The solution was stirred under argon for 24 hrs, dialyzed in deionized water and dried by lyophilizer for 3 days.

Series 2: Alpha-Hydroxy Heterobifunctional PEG Derivatives:

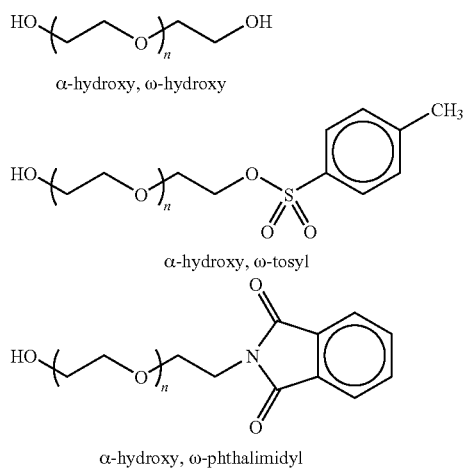

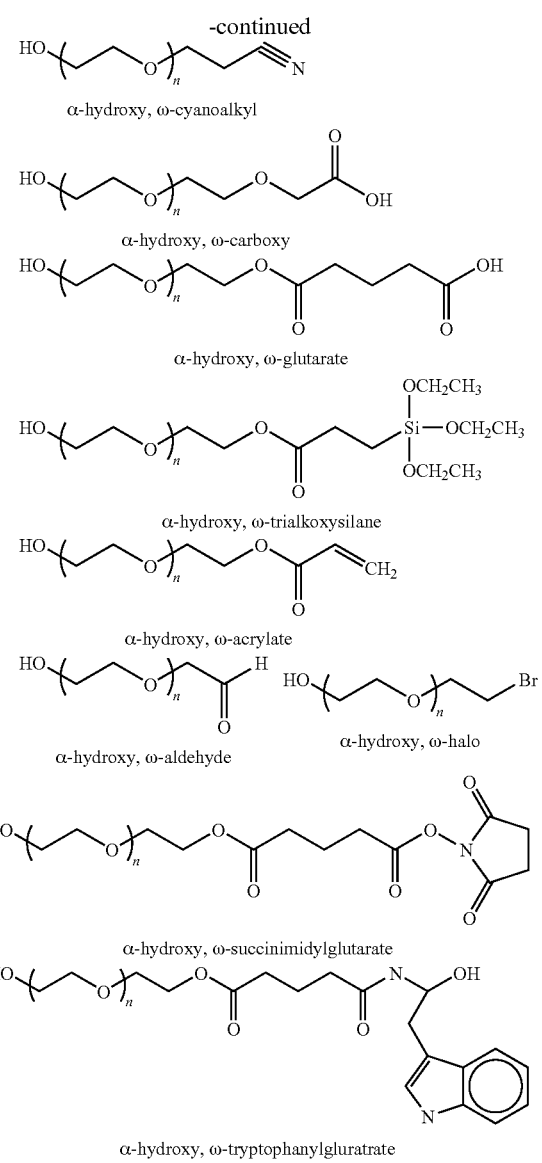

Series 2 Chemistry:

2.1. PEG is commercially available.

2.2. To synthesize α-hydroxy, ω-tosyl PEG, PEG (1 eq.) was dissolved in dry methylene chloride followed by addition of p-toluenesulfonylchloride (1 eq.) and triethylamine (1 eq.). The solution was stirred at room temperature for 48 hr, precipitated in cold hexane, collected by filtration and dried in vacuum oven for 24 hr.

2.3. To synthesize α-hydroxy, ω-phthalimidyl PEG, α-hydroxy, ω-tosyl PEG (1 eq.) from series 2.2 and potassium phthalimide (1.2 eq.) were dissolved in toluene and stirred at 50° C. for 20 hr. The solution was cooled down, filtered and the filtrate was precipitated in cold hexane, collected by filtration and dried in a vacuum oven for 24 hr.

2.4. To synthesize α-hydroxy, ω-cyanoalkyl PEGs, PEG (1 eq.) was dissolved in dry methylene chloride solution followed by the addition of fine sodium metal (1.2 eq.) and stirred for 12 hr at room temperature. Excess amount of acrylonitrile was added to the solution, stirred for 12 hr, filtered, and dried by rotary evaporation.

2.5. To synthesize α-hydroxy, ω-carboxy PEG, PEG (1 mol) was dissolved in dry THF, sodium (1.2 eq.) and naphthalene (1.2 eq.) were dissolved in dry THF and stirred under argon for 1 hr. The sodium/naphthalene solution was added dropwise to the PEG solution, the solution was stirred under argon for 4 hr. Ethyl bromoacetate (1.2 eq.) was then added and the solution was stirred under argon for 12 hr. The solution was filtered and the filtrate was precipitated in cold hexane, collected by filtration and dried in vacuum oven for 24 hr. The dried substance was dissolved in deionized water followed by addition of sodium hydroxide (1 eq.). The solution was stirred at 40° C. for two hr, extracted by methylene chloride for two times and evaporated by rotary evaporation.

2.6. To synthesize α-hydroxy, ω-glutarate PEG, PEG (1 eq.) was dissolved in dry THF followed by addition of glutaric anhydride (1.5 eq.) and glutaric acid (0.001 eq.). The solution was stirred at 70° C. for 48 hr, cooled down, precipitated in cold hexane, collected by filtration and dried in vacuum oven for 24 hr.

2.7. To synthesize α-hydroxy, ω-triethoxysilane PEG, α-hydroxy, ω-acrylate PEG (1 eq.) from series 2.8 was dissolved in dry THF followed by addition of triehyoxysilane (5 eq.) and chloroplatinic acid (a grain). The solution was stirred at 60° C. for 48 hr, cooled down, precipitated in cold hexane, collected by filtration and dried in vacuum oven for 24 hr.

2.8. To synthesize α-hydroxy, ω-acrylate PEG, PEG (1 eq.) was dissolved in dry THF followed by the addition of acryloyl chloride (1.5 eq.) and triethylamine (1.7 eq.). The solution was stirred at room temperature for 2 hr, filtered and the filtrate was precipitated in cold hexane, collected by filtration and dried in vacuum oven for 24 hr.

2.9. To synthesize α-hydroxy, ω-aldehyde PEG, PEG (1 eq.) was dissolved in DMSO and the solution was added dropwise to the acetic anhydride (20 eq.) and stirred at room temperature for 2 hr. Ether was then added to the solution and stirred for 5 min at room temperature and placed in the −20° C. freezer for 5 minutes to precipitate. The precipitate was collected by filtration and then dissolved in minimal amounts of methylene chloride and reprecipitated likewise twice by ether. The precipitate was dried in vacuum oven for 24 hr.

2.10. To synthesize α-hydroxy, ω-halo PEG, PEG (1 eq.) was dissolved in toluene followed by addition of triethylamine (1.2 eq.). The solution was stirred at 60° C. for 30 min followed by addition of thionyl bromide (1.2 eq.) and stirred at 60° C. for 1 hr. The hot solution was filtered through celite and the filtrate was kept in refrigerator at −4° C. for 24 hr. The precipitate was collected by filtration and dried in vacuum oven for 24 hr.

2.11. To synthesize α-hydroxy, ω-succinimidylglutrate PEG, α-hydroxy, ω-glutarate PEG (1 eq.) resulted from series 2.6 and dicyclohexylcarbodiimide (DCC 1.2 eq.) were dissolved in dry THF respectively. N-hydroxy succinimide (1.2 eq.) was added to the PEG solution followed by dropwise addition of DCC solution. The mixture solution was stirred at room temperature for 6 hr, filtered and the filtrate was precipitated in cold hexane, collected by filtration and dried in vacuum oven for 3 days and then stored under argon at −4° C. in the refrigerator.

2.12. To synthesize α-hydroxy, ω-tryptophanylglutrate PEG, α-hydroxy, w-succinimidylglutrate PEG (1 eq.) from series 2.11 was dissolved in DMF followed by addition of tryptophan (1.5 eq.). The solution was stirred under argon for 24 hrs, dialyzed in deionized water and dried by lyophilizer for 3 days.

Series 3: Alpha-Acrylate Heterobifunctional PEG Derivatives:

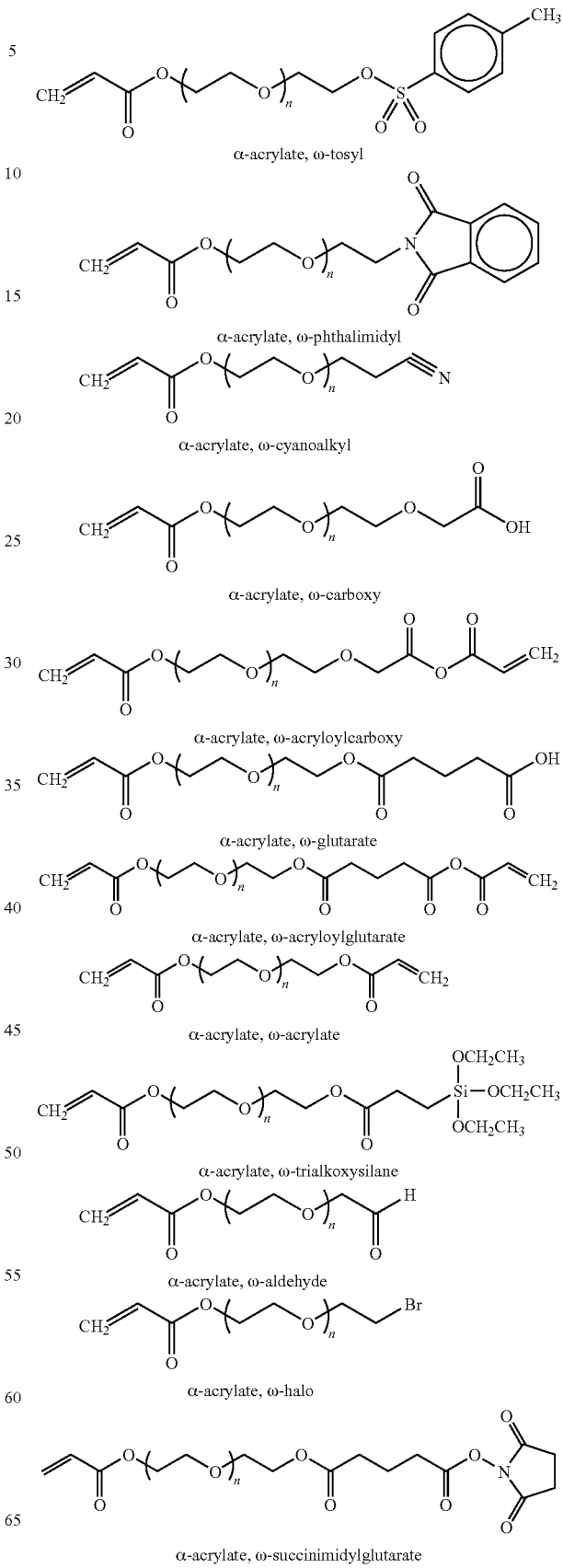

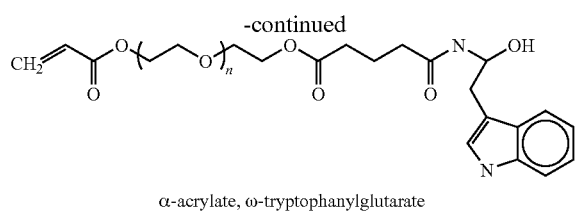

α-acrylate, ω-tryptophanylglutarate

Series 3 Chemistry:

3.1. To synthesize α-acylate, ω-tosyl PEG, α-hydroxy, ω-tosyl PEG (1 eq.) from series 2.2 was dissolved in dry THF followed by addition of acryloyl chloride (2 eq.) and triethylamine (2.2 eq.). The solution was stirred at room temperature for 2 hr, filtered and the filtrate was precipitated in cold hexane, collected by filtration and dried in vacuum oven for 24 hr.

3.2. To synthesize α-acylate, ω-phthalimidyl PEG, α-acylate, ω-tosyl PEG (1 eq.) from series 3.1 and potassium phthalimide (2 eq.) were dissolved in toluene and stirred at 50° C. for 20 hr. The solution was cooled down, filtered and the filtrate was precipitated in cold hexane, collected by filtration and dried in vacuum oven for 24 hr.

3.3. To synthesize α-acylate, ω-cyanoalkyl PEGs, α-hydroxy, ω-acrylate PEG (1 eq.) from series 2.8 was dissolved in dry methylene chloride solution followed by the addition of fine sodium metal (1.5 eq.) and stirred for 12 hr at room temperature. Excess amount of acrylonitrile was added to the solution, stirred for 12 hr, filtered, and dried by rotary evaporation.

3.4. To synthesize α-acylate, ω-carboxy PEG, α-hydroxy, ω-carboxy PEG (1 eq.) from series 2.5 was dissolved in dry THF followed by addition of acryloyl chloride (1.2 eq.) and triethylamine (1.5 eq.). The solution was stirred at room temperature for 2 hr, filtered and the filtrate was precipitated in cold hexane, collected by filtration and dried in vacuum oven for 24 hr.

3.5. To synthesize α-acylate, ω-acryloylcarboxy PEG, ω-carboxy PEG (1 eq.) from series 2.5 was dissolved in dry THF followed by addition of acryloyl chloride (3 eq.) and triethylamine (3.5 eq.). The solution was stirred at room temperature for 2 hr, filtered and the filtrate was precipitated in cold hexane, collected by filtration and dried in vacuum oven for 24 hr.

3.6. To synthesize α-acylate, ω-glutarate PEG, α-hydroxy, ω-glutarate PEG (1 eq.) from series 2.6 was dissolved in dry THF followed by addition of acryloyl chloride (1.2 eq.) and triethylamine (1.5 eq.). The solution was stirred at room temperature for 2 hr, filtered and the filtrate was precipitated in cold hexane, collected by filtration and dried in vacuum oven for 24 hr.

3.7. To synthesize α-acylate, ω-acryloylglutarate PEG, α-hydroxy, ω-glutarate PEG (1 eq.) from series 2.6 was dissolved in dry THF followed by addition of acryloyl chloride (3 eq.) and triethylamine (3.5 eq.). The solution was stirred at room temperature for 2 hr, filtered and the filtrate was precipitated in cold hexane, collected by filtration and dried in vacuum oven for 24 hr.

3.8. To synthesize α-acrylate, ω-acrylate PEG, PEG (1 eq.) was dissolved in dry THF followed by the addition of acryloyl chloride (3 eq.) and triethylamine (3.5 eq.). The solution was stirred at room temperature for 2 hr, filtered and the filtrate was precipitated in cold hexane, collected by filtration and dried in vacuum oven for 24 hr.

3.9. To synthesize α-acylate, ω-triethoxysilane PEG, α-hydroxy, ω-triethoxysilane PEG (1 eq.) from series 2.7 was dissolved in dry THF followed by the addition of acryloyl chloride (1.2 eq.) and triethylamine (1.5 eq.). The 17, solution was stirred at room temperature for 2 hr, filtered and the filtrate was precipitated in cold hexane, collected by filtration and dried in vacuum oven for 24 hr.

3.10. To synthesize α-acylate, ω-aldehyde PEG, α-hydroxy, ω-aldehyde PEG (1 eq.) from series 2.9 was dissolved in dry THF followed by the addition of acryloyl chloride (1.2 eq.) and triethylamine (1.5 eq.). The solution was stirred at room temperature for 2 hr, filtered and the filtrate was precipitated in cold hexane, collected by filtration and dried in vacuum oven for 24 hr.

3.11. To synthesize α-acylate, ω-halo PEG, α-hydroxy, ω-halo PEG (1 eq.) from series 2.10 was dissolved in dry THF followed by the addition of acryloyl chloride (1.2 eq.) and triethylamine (1.5 eq.). The solution was stirred at room temperature for 2 hr, filtered and the filtrate was precipitated in cold hexane, collected by filtration and dried in vacuum oven for 24 hr.

3.12. To synthesize α-acylate, ω-succinimidylglutrate PEG, α-hydroxy, ω-succinimidylglutrate PEG (1 eq.) from series 2.11 was dissolved in dry THF followed by the addition of acryloyl chloride (1.2 eq.) and triethylamine (1.5 eq.). The solution was stirred at room temperature for 2 hr, filtered and the filtrate was precipitated in cold hexane, collected by filtration and dried in vacuum oven for 24 hr.

3.13. To synthesize α-acylate, ω-succinimidylglutrate PEG, α-hydroxy, ω-tryptophanylglutrate PEG (1 eq.) from series 2.12 was dissolved in dry THF followed by the addition of acryloyl chloride (1.2 eq.) and triethylamine (1.5 eq.). The solution was stirred at room temperature for 2 hr, filtered and the filtrate was precipitated in cold hexane, collected by filtration and dried in vacuum oven for 24 hr.

Series 4: Homo-Bifunctional PEG Derivatives:

Modified PEGS wherein the α and the ω termini have the same functional groups can also be fabricated using the same approach. Thus, using the chemistries described herein, bis-acrylate, bis-tosylate, bis-phthalimidyl, bis-cyanoalkyl, bis-carboxylate, bis-acryloylcarboxylate, bis-glutarate, bis-acryloylglutarate, bis-trialkoxysilane, bis-aldehyde, bis-N-succinimidyl, and bis-tryptophanylglutarate derivatives can be fabricated.

Thus, according to the present invention, a polymer matrix, preferably gelatin, is modified to contain one or more of the modified PEG molecules disclosed herein. The PEG molecule may be bis-modified, using the same type of moiety. Or, the α-terminus of the PEG may have a different moiety than the ω-terminus. Both versions of the modified PEG molecules, as incorporated into a hydrogel, fall within the scope of the present invention.

Interpenetrating Network Hydrogels (IPNs):

The above described PEG-modified hydrogels can also be used as a first polymer matrix in an interpenetrating network of two distinct polymer matrices. In this aspect of the invention, the PEG-modified hydrogels as described above are admixed with a polymerizable mixture of monomers. A polymerization reaction is then initiated, whereby the mixture of monomers polymerizes in situ, thereby forming a second polymer matrix that interpenetrates with the first polymer matrix.

It is much preferred that the plurality of monomers that forms the second polymer matrix is polymerizable by a means other than chemical initiation. Chemically polymerizable monomers are, however, within the scope of the invention. In the preferred embodiment, the monomers are photopolymerizable. Thus, the monomers are admixed with the first polymer matrix. The mixture is then exposed to a suitable wavelength of radiation (e.g., infrared, visible, or ultraviolet) that will result in a photo-initiated polymerization reaction. The source for the radiation can be any source that generates radiation of the required wavelength, such as lamps (incandescent, fluorescent, ion discharge, etc.), lasers ($CO_2$, Ne—Ne, etc.), and light-emitting diodes.

The preferred photopolymerizable monomers are acrylates, diacrylates, and poly(acrylates) (including PEG-acrylates, PEG-diacrylates, and TMPTA), acrylic acid, and acryloyl halides, such as acryloyl chloride, and mixtures thereof. When a plurality of different monomers is admixed with the first polymer matrix, the polymerization reaction will, of course, result in the second polymer matrix being a co-polymer. Thus, the second polymer matrix may comprise a homopolymer matrix or a co-polymer matrix of any description (e.g., alternating, block, or graft co-polymers).

Figure 6:
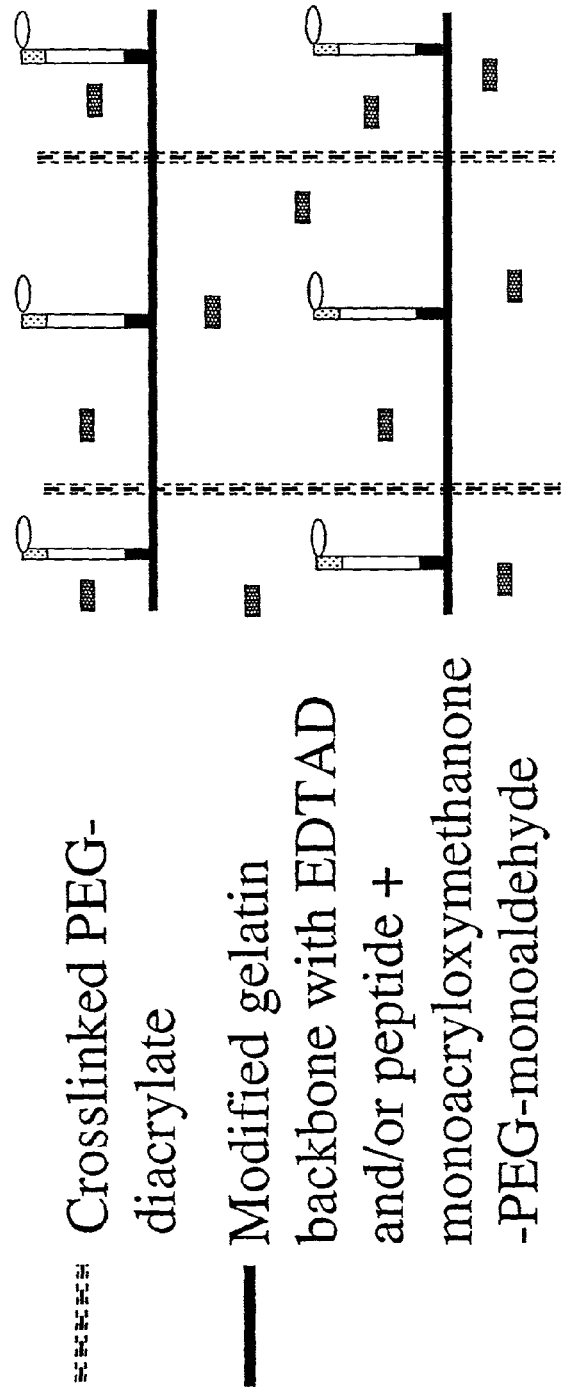
FIG. 6. A schematic representation of an interpenetrating network hydrogel according to the present invention.

FIG. 6 is a schematic representation of interpenetrating network hydrogels according to the present invention. The gels can contain living cells or pharmacologically-active agents, or both.

EXAMPLES

The following Examples are included herein solely to provide a more complete and consistent understanding of the invention disclosed and claimed herein. The Examples do not limit the scope of the invention in any fashion.

Example 1

Synthesis and Characterization of Heterobifunctional PEGs

All reagents were purchased from Sigma-Aldrich (St. Louis, Mo.) unless stated otherwise. A summary of the chemical reactions and structure of critical intermediates and final products is presented in FIG. 1.

To synthesize α-methyl-ω-acrylate PEGs (M-PEG), monomethoxy PEGs (2 kDa or 5 kDa, purchased from Fluka, a division of Sigma-Aldrich) were dissolved in dry tetrahydrofuran (THF) solution followed by the addition of triethylamine (TEA, 2 eq.) and acryloyl chloride (AC, 4 eq.)[14] at room temperature under Ar for 10 min, filtered, dried by rotary evaporation, re-dissolved in $CH_2Cl_2$, and precipitated in cold hexane. The final product was filtered, dried, and stored in vacuo at room temperature.

To synthesize α-cyanoethyl-ω-acrylate-PEGs (CN-PEG), PEG-diols (2 kDa or 5 kDa) (1 eq.) were dissolved in dry $CH_2Cl_2$ solution followed by the addition of fine sodium metal (2 eq.) stirred for 12 hr at room temperature. An excess amount of acrylonitrile was added into the solution[15, 16], stirred for 12 hr, filtered, and dried by rotary evaporation. The product thus formed (i.e., α-nitrile-ω-hydroxy-PEG) was dissolved in dry THF, followed by the addition of TEA (2 eq.) and AC (4 eq.). The solution was stirred under Ar for 10 min at room temperature. Triethylammonium chloride was removed by filtration and the solvent was removed by rotary evaporation. The final product was re-dissolved into $CH_2Cl_2$, precipitated in cold hexane, filtered, and stored in vacuo at room temperature.

To synthesize α-carboxyl-ω-acrylate-PEGs (COOH-PEG), sodium (3.5 eq) in mineral oil was dried, dissolved in dried THF with naphthalene (3.5 eq), and stirred for 1 hr under Ar at room temperature.[17] The sodium/naphthalene solution thus formed was added drop wise into PEG-diols (2 kDa or 5 kDa) (1 eq.) dissolved in dried THF under Ar for 4 hr. Ethyl bromoacetate (4 eq) was added to the ionized PEG solution, stirred for 12 hr, filtered, precipitated in cold hexane, and re-dissolved in distilled water (1 eq) with sodium hydroxide (3 eq)[18], followed by reflux for 24 hr at room temperature. Solvent was removed by rotary evaporation and the solid was re-dissolved in $CH_2Cl_2$, filtered, precipitated in cold hexane, dried in vacuo. The solid of mainly α-carboxyl-ω-hydroxyl-PEGs (1 eq.) was dissolved in dried THF followed by the addition of TEA (2 eq.) and AC (4 eq), stirred at room temperature for 10 min under Ar, filtered, precipitated in cold hexane, filtered, dried, and stored in vacuo at room temperature.

To synthesize α-phthalimide-ω-acrylate-PEGS (PT-PEG), PEG-diols (2 kDa or 5 kDa) (1 eq.) were dissolved in dry $CH_2Cl_2$ solution followed by the addition of TEA (4 eq.) and p-toluenesulfonyl chloride (2 eq.)[19] and stirred under Ar for 8 hr at room temperature. Solvent was removed by rotary evaporation to obtain yellowish white solids. This mixture of PEG-diols, α-hydroxyl-ω-tosyl-PEGs, and bis-tosyl-PEG (1 eq.) was dissolved in dry THF, followed by the addition of TEA (2 eq.) and AC (4 eq.), stirred at room temperature under Ar for 10 min, filtered to remove triethylammonium chloride, dried via rotary evaporation to remove solvents, re-dissolved into $CH_2Cl_2$, and precipitated in cold hexane. The solid product (mainly α-tosyl-ω-acrylate-PEG) was filtered, dried in vacuo, dissolved (1 eq.) in $CH_2Cl_2$, followed by the addition of potassium phthalimide (3 eq.)[20] and refluxed for 18 hr. The solution was filtered, dried via rotary evaporation to remove solvents, re-dissolved into $CH_2Cl_2$, precipitated in cold hexane, filtered, dried, and stored in vacuo at room temperature.

All intermediates and final products were analyzed with $^1H$- and $^{13}C$-NMR with samples dissolved in $CDCl_3$ and with a reverse-phase HPLC system (10% to 100% acetonitrile at a flow rate of 1 ml/min in 60 min with a Jordi 500 Å column on a Gilson system) coupled to an automated multi-sample sampler-fraction collector. Detectors included UV/Vis (200 and 254 nm), photodiode array, and evaporative light scattering detectors.

The above-described heterobifunctional PEGs (hPEGs) were employed as a component in the formation of hydrogels to investigate the influence of hPEG concentration, molecular weight, and terminal moiety on the surface hydrophilicity and cell interaction. The hPEGs were utilized in the hydrogel formulation following procedures described hereinabove. See also references (10-13). The network thus formed is a random copolymer of Ac, TMPTA, and hPEG, with, for example, an acrylate ω-terminal and an α-terminal of a different chemical moiety (XPEGmA).

Specifically, XPEGmAs were grafted to a gelatin polymer matrix with various dangling terminal functional groups and incorporated throughout the polymer matrix by copolymerizing the acrylate terminal into a randomly polymerized network of Ac and TMPTA.[10-13] This type of polymer network containing M-PEG is nonionic, low swelling, glassy when dry, optically transparent, and colorless.[10-13] In spite of the relatively high mass fraction of M-PEGs present, minimal swelling was observed for the polymer due to the highly cross-linked and hydrophobic nature of the TMPTA network. Differential scanning calorimetry analysis showed that these materials are completely amorphous and the M-PEG component is completely phase-mixed in the cross-linked TMPTA matrix.[10]

The surface hydrophilicity of XPEGmA-co-Ac-co-TMPTA networks was quantified with an underwater air bubble captive system. The hydrogel was completely suspended in water that was maintained at a physiologically-relevant temperature of 37.5° C. An air bubble was placed at the down side of the gel and the contact angle was measured using a modified computer-assisted video contact angle system (AST Inc). Measurement was made at six randomly selected areas, averaged, and repeated three times on three different polymer samples (n=3). Because the air bubble contact angle was measured through the aqueous phase and performed under water, the value obtained is essentially the water-receding contact angle; furthermore, the higher the contact angle, the higher is the hydrophilicity of the film.

The gels so formed were then evaluated for their interaction with cultured cells. Human neonatal dermal fibroblasts at a concentration of 75,000 per 1 ml of Fibroblast Basal Medium with human fibroblast growth factor-b (0.5 mg/ml), insulin (0.5 mg/ml), and 5% fetal bovine serum (Clonetics, San Diego, Calif.) were incubated with the XPEGmA-co-Ac-co-TMPTA network. At 2, 24, and 48 hr thereafter, adherent cell morphology and density were manually quantified using a computer-assisted video analysis system coupled to an inverted light microscope.

All experimental results are expressed in mean±standard deviation (S.D.). Each sample was independently repeated three times (n=3). Comparative analyses were performed with Statview® 4.5 using analysis of variance and Fisher's protected least significant difference test at 95% confidence level ($p<0.05$).

$^{13}$C-NMR chemical shifts for M-PEG, CN-PEG, COOH-PEG, and PT-PEG intermediates and final products synthesized from 2 kDa PEG precursors are listed in Table 1.

group, the assigned carbon showed signals at the corresponding chemical shift. For the final acrylated product with a general chemical structure of $X—CH_2CH_2O(CH_2CH_2O)_nCH_2CH_2OCOCHCH_2$, where X is: $—OCH_3$, $—CN$, $—OCH_2COOH$, or phthalimide, three unique chemical shifts were observed that correspond to the three carbons of the acrylate group. Specifically, the chemical shifts for $—COO—$ stretch and $—CHCH_2$ stretch were observed at 165.3 to 170.6 and 128.0 to 130.9 ppm, respectively. In addition, appropriate chemical shifts were observed for the assigned carbon for each terminal group (Y). Similar NMR results were obtained when 5 kDa PEGs were utilized in lieu of 2 kDa PEGs as precursors in the synthesis scheme for all compounds shown in Table 1.

Figures 2A, 2B:
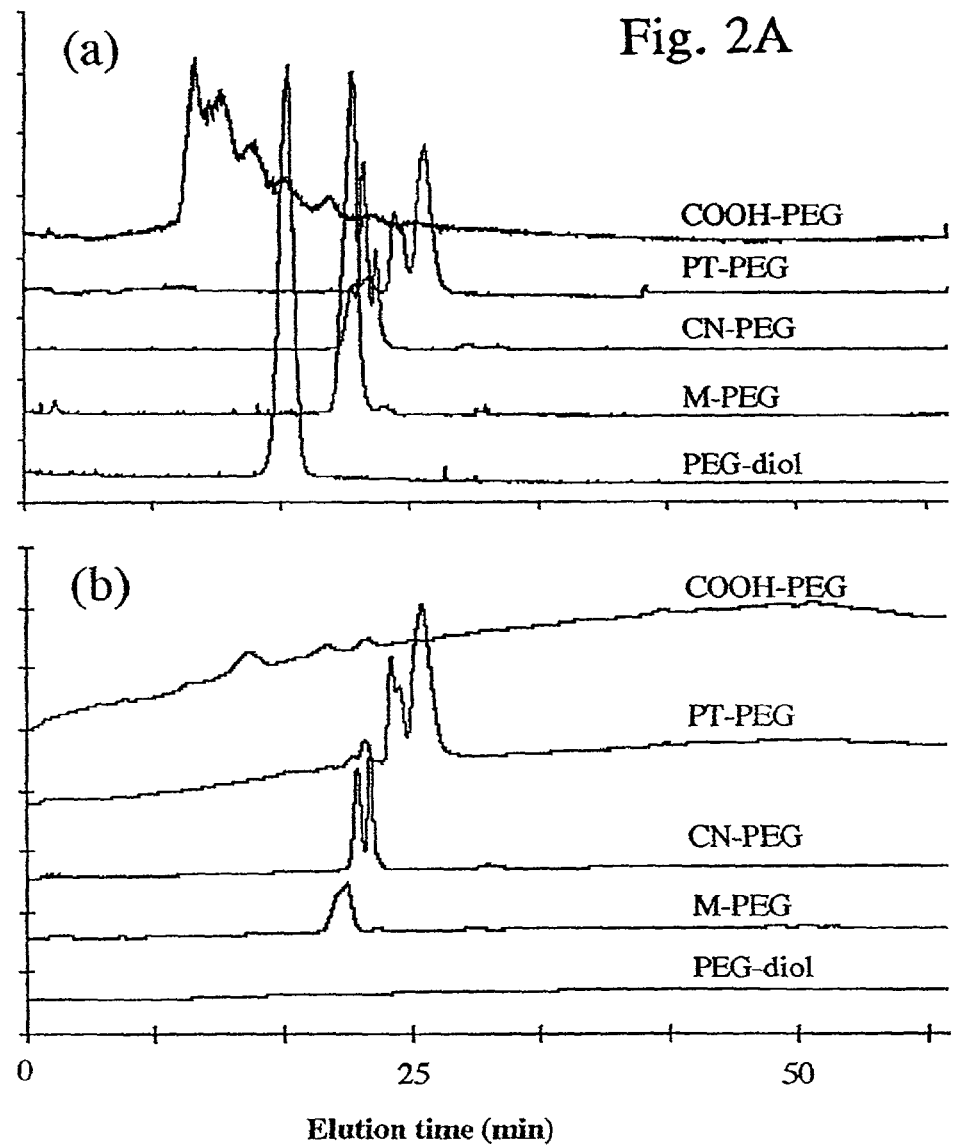

To determine percent conversions of the final product of M-PEG, CN-PEG, COOH-PEG, and PT-PEG, HPLC analyses performed (Table 2 and FIGS. 2A and 2B) from various HPLC detectors were utilized to elucidate the chemical structure of each individual peak of a given chromatogram. In addition, each fraction was collected with an automated fraction collector and re-analyzed using $^1$H and $^{13}$C NMR to ascertain further the chemical composition(s) of each collected fraction. Results showed 100% conversion for M-PEG from the PEG starting material. CN-PEG showed approximately 65% conversion with no other acrylated side products.

TABLE 1

$^{13}$C-NMR chemical shifts (ppm) for M-PEG, CN-PEG, COOH-PEG, and PT-PEG critical intermediates and final products synthesized from 2K Da PEG-diol precursors Chemical Shifts of Designated Carbon (in superscript) with Compounds with the Following General Structure

| n-CH$_2$ | C$^{\alpha 1}$ | C$^{\beta 1}$ | C$^{\alpha 2}$ | C$^{\beta 2}$ | C$^{(1)}$ | C$^{(2)}$ | C$^{(3)}$ | C$^{(4)}$ | C$^{(5)}$ | C$^{(6)}$ | C$^{(7)}$ | Chemical Group of Terminal Y |
|---|---|---|---|---|---|---|---|---|---|---|---|---|
| \multicolumn{13}{c}{$Y—C^{(\alpha 1)}H_2C^{(\beta 1)}H_2O(CH_2CH_2O)_nC^{(\beta 2)}H_2C^{(\alpha 2)}H_2OH$} |
| 70.4 | 61.3 | 72.4 | 61.3 | 72.4 | — | — | — | — | — | — | — | —OH |
| 70.5 | 30.3 | 71.2 | 62.9 | 72.3 | — | — | — | — | — | — | — | —Br |
| 70.4 | 19.8 | 66.2 | 62.3 | 72.4 | 119.0 | — | — | — | — | — | — | —C$^{(1)}$N |
| 70.4 | 68.2 | 70.2 | 61.3 | 72.4 | 53.7 | 171.2 | — | — | — | — | — | —OC$^{(1)}$H$_2$C$^{(2)}$OOH |
| 70.4 | 64.4 | 71.8 | 61.6 | 69.7 | 58.2 | — | — | — | — | — | — | —OC$^{(1)}$H$_3$ |
| 70.5 | 68.6 | 69.2 | 61.6 | 72.5 | 163.6 | 114.7 | 131.6 | 130.0 | 21.8 | — | — | 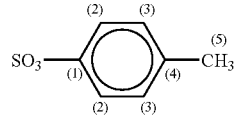 |
| \multicolumn{13}{c}{$Y—C^{(\alpha 1)}H_2C^{(\beta 1)}H_2O(CH_2CH_2O)_nC^{(\beta 2)}H_2C^{(\alpha 2)}H_2OC^{(1)}OC^{(2)}HC^{(3)}H_2$} |
| 70.5 | 64.6 | 71.1 | 63.9 | 68.2 | 165.3 169.5 | 130.6 | 128.2 | 58.2 | — | — | — | —OC$^{(4)}$H$_3$ |
| 70.4 | 18.6 | 66.5 | 64.3 | 68.7 | 165.9 169.2 | 130.6 | 128.0 | 117.7 | — | — | — | —C$^{(4)}$N |
| 70.5 | 68.5 | 70.8 | 64.6 | 68.4 | 166.0 169.5 | 130.9 | 128.2 | 53.6 | 170.3 | — | — | —OC$^{(4)}$H$_2$C$^{(5)}$OOH |
| 70.5 | 37.2 | 67.8 170.6 | 63.8 | 68.8 | 167.8 | 130.9 | 128.2 | 168.0 | 132.1 | 123.1 | 133.9 | 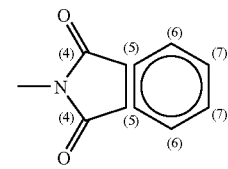 |

For all samples, the methyl stretch and the "b" carbon of the PEG chains were observed at approximately 68 to 72 ppm; whereas, the "a" carbon shift was highly dependent on the terminal group (Y). For compounds with a general structure of $HOCH_2CH_2O(CH_2CH_2O)_nCH_2CH_2—Y$, where Y is $—OH$, $—Br$, $—CN$, $—OCH_2COOH$, $—OCH_3$, or tosyl PT-PEG showed an approximate 65% conversion with about 5% of the final product containing another acrylate side-product (e.g., α-tosyl-ω-acrylate-PEG). COOH-PEG showed an approximate 60% conversion with an additional 10% of other acrylated side-products (e.g., α-hydroxyl-ω-acrylate-PEG and bis-acrylate-PEG).

TABLE 2

Comparison of HPLC retention time, normalized peak area, and percent conversion for M-PEG, CN-PEG, COOH-PEG, and PT-PEG synthesized from 2K Da PEG-diol precursors

| PEG Product | Retention Time (min) | Normalized Peak Area | Conversion Factor (%) | UV Signal | PEG Derivative Identification |
|---|---|---|---|---|---|
| PEG-diol | 16 | 1.0 | 1 | no | α-methyl-ω-hydroxyl |
| M-PEG | 21 | 1.0 | 100 | strong | α-methyl-ω-acrylate |
| CN-PEG | 21 | 1.1 | 13 | strong | bis-ethylcyano |
|  | 23 | 5.2 | 63 | strong | α-ethylcyano-ω-acrylate |
|  | 24 | 2.0 | 24 | no | α-nitrile-ω-hydroxy |
| COOH-PEG | 11 | 2.5 | 14 | no | bis-carboxyl |
|  | 13 | 2.3 | 13 | no | α-carboxyl-ω-hydroxyl |
|  | 15 | 10.1 | 57 | weak | α-carboxyl-ω-acrylate |
|  | 16 | 1 | 6 | no | bis-hydroxyl |
|  | 19 | 1.2 | 7 | weak | α-hydroxyl-ω-acrylate |
|  | 23 | 0.6 | 3 | weak | bis-acrylate |
| PT-PEG | 22 | 2.0 | 7 | weak | α-tosyl-ω-acrylate |
|  | 24 | 8.1 | 26 | strong | bis-phthalimide |
|  | 26 | 19.5 | 64 | strong | α-phthalimide-ω-acrylate |

These results validate the synthesis of the XPEGmAs that were employed as a main component in the hydrogel synthesis. Based on the gel synthesis scheme, hPEG containing one or more acrylate groups will be covalently incorporated into the network; whereas, those without any acrylate groups will be removed from the network after the equilibration step in water as a part of the network formation procedure. Although the final product of each XPEGmA was not further purified prior to the polymer synthesis, the low concentration of other acrylated side products plays a minimal role in the network composition.

These heterobifunctional intermediates and final products of XPEGmA are stable under storage in vacuo at room temperature and can be modified further by a broad range of chemical methods for various applications. For example, the phthalimide group is a good protecting group that can be hydrolyzed to form primary amines.

Figures 3A, 3B:
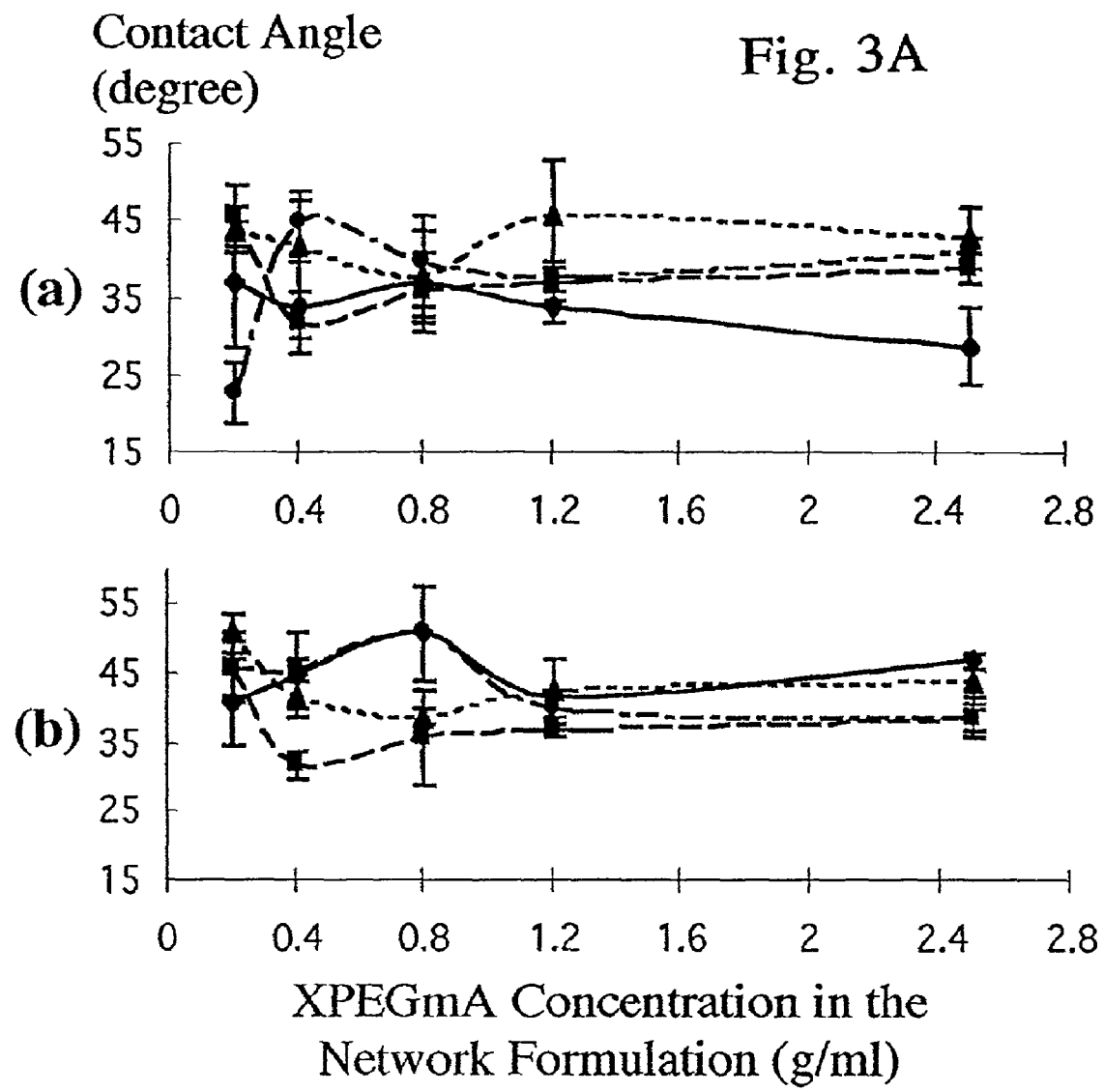
FIGS. 3A and 3B. Surface hydrophilicity of the XPEGmA-co-Ac-co-TMPTA network containing XPEGmA of various concentration, terminal moiety, and molecular weight. (3A) 2 KDa XPEGmA and (3B) 5 KDa XPEGmA. Legend: ♦=M-PEG; ■=CN-PEG; ▲=COOH-PEG; and ●=PT-PEG.

A previously developed polymer network formulation was adopted to elucidate the effect of the PEG chemistry on the surface characteristics of the resulting hydrogels. Polymer networks containing various XPEGmAs at several concentrations and different molecular weights were transparent or translucent. The network surface hydrophilicity was quantified using an under water contact angle system and was found to be dependent of three factors: the molecular weight of the starting material PEG, the dangling terminal functional group, and the concentration of the XPEGmA in the network (see Table 3 and FIGS. 3A and 3B).

TABLE 3

Surface hydrophilicity of the XPEGmA-co-Ac-co-TMPTA network containing XPEGmA of various concentration, molecular weight, and terminal moiety

| XPEGmA type | XPEGmA concentration in the network formulation (g/ml) | | | | |
|---|---|---|---|---|---|
|  | 0.2 | 0.4 | 0.8 | 1.25 | 2.5 |
| 2K (Da) |  |  |  |  |  |
| M-PEG | 37 ± 8 | 34 ± 6 | 37 ± 4 | 34 ± 2 | 29 ± 5 |
| CN-PEG | 46 ± 4 | 32 ± 2 † | 36 ± 5 † | 37 ± 2 † | 39 ± 2 † § |
| COOH-PEG | 44 ± 3 | 42 ± 6 | 38 ± 6 † | 46 ± 7 § | 43 ± 4 § |
| PT-PEG | 23 ± 4 § | 45 ± 4 † § | 40 ± 6 † | 38 ± 2 † | 41 ± 2 † § |
| 5K (Da) |  |  |  |  |  |
| M-PEG | 41 ± 6 | 45 ± 6 ‡ | 51 ± 7 ‡ | 42 ± 5 ‡ | 47 ± 1 ‡ |
| CN-PEG | 46 ± 5 | 32 ± 2 † § | 36 ± 7 † § | 37 ± 1 † § | 39 ± 3 † § |
| COOH-PEG | 51 ± 3 ‡ § | 42 ± 2 † | 39 ± 1 † § | 43 ± 4 † | 44 ± 4 † |
| PT-PEG | 46 ± 4 ‡ | 46 ± 1 | 51 ± 7 | 40 ± 3 † | 39 ± 2 † § |

First, when a given concentration of XPEGmA containing a given dangling terminal group in the network was considered, an increase in the molecular weight of the terminal group significantly lowered the hydrophilicity of networks containing M-PEG (0.4 to 2.5 g/ml), COOH-PEG (0.2 g/ml), or PT-PEG (0.2 g/ml). For other networks, the molecular weight of XPEGmA did not significantly affect the hydrophilicity.

Second, the different terminal moiety of XPEGmA showed a variable effect on the surface hydrophilicity when compared with that of M-PEG of given molecular weight and concentration.

Third, the XPEGmA concentration in the network formulation showed various correlations with hydrophilicity. Because XPEGmA was employed in the network formation without further purification, the potential effect of differential percent conversion of acrylated hPEG on surface hydrophilicity must be addressed. M-PEG showed a 100% conversion and the network containing M-PEG demonstrated no changes in surface hydrophilicity with increasing M-PEG concentration. Whereas for other XPEGmAs, various correlations among hydrophilicity and the type, percent conversion (ca. 60 to 100%), and concentration were observed. Hence, it was concluded that the percent conversion of XPEGmA within 60 to 100% did not affect the dependency of XPEGmA concentrations on hydrophilicity. These analyses determined that the network surface hydrophilicity was predominately influenced by the XPEGmA concentration in the network formulation with the molecular weight and the terminal moiety playing lesser roles.

Next, XPEGmA-co-Ac-co-TMPTA networks containing various XPEGmAs at several concentrations were employed to determine the effect of surface characteristics of the gel on human fibroblast adhesion. All adherent cells showed extensive pseudopodial extension and cytoplasmic spreading, with some cells exhibiting polar cell body morphology. The results (see Table 4) showed that adherent cell density was primarily dependent on the XPEGmA concentration in the network formulation. Specifically, adherent cell density decreased with increasing XPEGmA concentration at all culture time. No adherent cell was observed on networks containing XPEGmA concentration between 1.25 to 2.5 g/ml at all culture times. These trends were independent of the XPEGmA molecular weight and terminal moiety. No direct mechanistic correlation can be made between network surface hydrophilicity and adherent cell density because several interrelated complex parameters (e.g., XPEGmA chemicophysical properties, adsorption of serum adhesion-mediating proteins, etc.) contribute to these two phenomena. However, the adherent cell density decreased with increasing XPEGmA concentration for all samples.

TABLE 4

Adherent human dermal fibroblast density on the XPEGmA-co-Ac-co-TMPTA network containing XPEGmA of various concentration, molecular weight, and terminal moiety

| XPEGmA type | Culture Time (hr) | | | | | | | | | | | | | | |
|---|---|---|---|---|---|---|---|---|---|---|---|---|---|---|---|
| | 2 hr | | | | | 24 hr | | | | | 48 hr | | | | |
| | XPEGmA concentration in the network formulation (g/ml) | | | | | | | | | | | | | | |
| | 0.2 | 0.4 | 0.8 | 1.25 | 2.5 | 0.2 | 0.4 | 0.8 | 1.25 | 2.5 | 0.2 | 0.4 | 0.8 | 1.25 | 2.5 |
| 2K (Da) | | | | | | | | | | | | | | | |
| M-PEG | 3 ± 2 | 3 ± 2 | 0 | 0 | 0 | 5 ± 2 | 2 ± 1 | 0 | 0 | 0 | 3 ± 2 | 4 ± 2 | 1 ± 1 | 0 | 0 |
| CN-PEG | 5 ± 4 | 2 ± 1 | 1 ± 1 | 0 | 0 | 3 ± 2 | 4 ± 3 | 1 ± 1 | 1 ± 1 | 0 | 5 ± 34 | 4 ± 3 | 3 ± 1 | 5 ± 2 | 0 |
| COOH-PEG | 2 ± 1 | 1 ± 0 | 1 ± 1 | 0 | 0 | 3 ± 1 | 2 ± 1 | 6 ± 4 | 0 ± 0 | 0 | 3 ± 2 | 1 ± 1 | 1 ± 1 | 1 ± 1 | 0 |
| PT-PEG | 2 ± 1 | 2 ± 1 | 1 ± 1 | 1 ± 0 | 0 | 1 ± 0 | 3 ± 2 | 3 ± 2 | 0 | 0 | 3 ± 1 | 2 ± 1 | 3 ± 3 | 0 ± 0 | 0 |
| 5K (Da) | | | | | | | | | | | | | | | |
| M-PEG | 3 ± 1 | 3 ± 2 | 0 | 0 | 0 | 3 ± 3 | 3 ± 2 | 1 ± 1 | 0 | 0 | 2 ± 1 | 3 ± 2 | 1 ± 1 | 0 | 0 |
| CN-PEG | 2 ± 2 | 1 ± 1 | 1 ± 0 | 0 | 0 | 4 ± 3 | 5 ± 4 | 0 ± 0 | 2 ± 1 | 0 | 3 ± 2 | 3 ± 2 | 0 ± 0 | 2 ± 2 | 0 |
| PT-PEG | 3 ± 1 | 1 ± 0 | 0 ± 0 | 0 | 0 | 2 ± 1 | 2 ± 2 | 0 ± 0 | 0 | 0 | 3 ± 1 | 3 ± 2 | 1 ± 1 | 0 | 0 |
| COOH-PEG | 4 ± 0 | 1 ± 1 | 1 ± 0 | 0 | 0 | 4 ± 2 | 2 ± 1 | 1 ± 0 | 1 ± 0 | 0 | 2 ± 1 | 3 ± 1 | 1 ± 0 | 0 ± 0 | 0 |

All values are expressed in ×100 cells/mm$^2$ (rounded-off for clarity, mean ± S.D., n = 3).

The results of this Example show that the presence of two distinct chemical moieties (i.e., carboxylic acids of the polyacrylic acid backbone and the distinct functional group at the dangling terminus of XPEGmA grafted at the pendent chain configuration) within the hydrogels can be employed to bind (covalently) two or more distinct types of biofunctional molecules such as peptides and pharmaceutics by employing distinct chemical methodologies. Furthermore, the high content of PEGs in this system reduced protein adsorption and effectively eliminated nonspecific cell adhesion that would occur as a result, thus permitting the modulating of cellular function mediated uniquely by the multiple immobilized biofunctional agent (10-13). The invention thus provides multifunctional hydrogels that can be used, for example, to study complex biological systems and to deliver therapeutic agents locally and systemically.

Example 2

Drug Release Kinetics

This Example explores the swelling and drug release kinetics of various gelatin-based hydrogels. The hydrogels were cross-linked by various means, and contained various modifications of the gelatin backbone. The effect of pH on the drug release kinetics of these gels was also investigated.

As noted above, cross-linking gelatin produces a hydrogel of high molecular weight and reduces or prevents gelatin dissolution. The cross-linking agents used in this Example were: 0.1%, 0.01%, and 0.001% (v/v) glutaraldehyde aqueous solutions, and self-cross-linking via liquid nitrogen immersion followed by baking. The backbone modifications to the gelatin were the addition of polyethylene glycol (PEG) or ethylenediaminetetraacetic dianhydride (EDTAD) or both. PEG has low immunogenicity and cytotoxicity. EDTAD has low toxicity and the lysyl residues of gelatin can be modified with EDTAD in a relatively fast reaction following facile procedures. See Hwang & Damodaran (1996) J. Agric. Food. Chem. 44:751-758. Also, modifying gelatin with EDTAD introduces polyanionic molecules into the gelatin chain, thereby improving the swelling capability of the gelatin hydrogels. The pHs investigated in this Example were pH 4.5, pH 7.0 and pH 7.4. Based on the swelling/degradation and drug release kinetics of these hydrogels under the stated conditions and in vivo analysis, these hydrogels are suitable as support matrices for the regeneration of rat neutral stem cells and as a drug carrier in mediating inflammation in vivo.

PEG diol (Aldrich, $M_n$ 2 kD) was converted to PEG dialdehyde (PEGdial) by reacting PEG with acetic anhydride in DMSO in a molar ratio of 1:80:140 for 4 hours at 25° C. The composition of PEG dialdehyde was confirmed using the reverse-phase HPLC system and parameters as described in Example 1. This reaction produces a mixed product of PEG monoaldehyde and PEG dialdehyde. PEG dialdehyde had an elution time of approximately 11.5 min. and was approximately 80 wt % of the final product.

The lysyl amino groups of gelatin samples (Sigma, St. Louis, Mo.; Type A, from porcine skin, 300 bloom, cell culture tested) were modified by PEGdial to form PEG-modified gelatin (PG). Gelatin samples were also modified using EDTAD (Aldrich) to form EDTAD-modified gelatin (EG). Still further gelatin samples were modified with PEGdial and EDTAD to yield PEG-modified-EDTAD-modified gelatin (P/EG). PG or P/EG was created by adding PEGdial dissolved in 10 ml of $H_2O$ (Milli-Q synthesis, 18.2 MΩ-cm, Millipore) and NaCNBH$_3$ dissolved in 10 ml of $H_2O$ separately and simultaneously to a 5% (w.v) gelatin or EG solution at 50 to 60° C. for 24 hours in a wt ratio of gelatin/EG:PEGdial:NaCNBH$_3$ of (1:0.66:0.186). The theoretical maximum percent modification using this method is 100% modification of gelatin lysyl residues, based on an average 300 bloom gelatin molecular weight and average lysine content of the gelatin. See, e.g., Merck Index, 12$^{th}$ Ed. (1996) #4388, p. 742. EG was created by adding EDTAD to a 1% (w/v) gelatin solution at pH 10, 40° C. for 3 hours in a wt ratio of gelatin:EDTAD of 1:0.034. The theoretical maximum percent modification of gelatin lysyl residues using this method is 38%. Thus, modifications larger than this indicate that both functional groups of the added EDTAD have bonded to lysyl residues in the gelatin, thereby cross-linking the gelatin chains. The level of gelatin modification was quantified using the 2,4,6-trinitrobenzene sulfonic acid spectrophotometric method. See Hwang & Damodaran, supra, and Offner & Bubnis (1996) Pharm. Res. 13:1821-1827.

To make the hydrogels, 10% (w/v in H$_2$O) solutions of gelatin (G), 10% PG, 40% EG and 60% P/EG were heated to approximately 70° C. and poured into petri dishes (60×15 mm, Cole-Parmer) to a thickness of 6 mm and allowed to set at room temperature overnight. Hydrogels were cut into 1 cm diameter circular discs or into 0.5×0.5 cm squares, and cross-linked with 0.1, 0.01 or 0.001% (v/v in H$_2$O) glutaraldehyde (Electron Microscopy Sciences, EM grade, 10% (v/v) aqueous solution) for 6 hours with gentle shaking. Cross-linked hydrogels were washed with H$_2$O ten times for 3-5 min. Washed hydrogels were left overnight in H$_2$O for continued leaching of the gluteraldehyde. Hydrogels were then dried at room temperature in ambient air for 48 hours and weighed. Separately, hydrogels of 10% by wt gelatin were dried in ambient air for 48 hours, frozen in liquid nitrogen for 30 seconds to 1 minute and then baked at 130-135° C. for 8.5 hours (self-cross linked; LN$_2$-baked G). Not all hydrogel formulations withstood the cross-linking, washing and drying steps, mainly due to hydrolysis. The hydrogel formulations that were included in the swelling/degradation and in vitro drug release studies were the 0.1% glutaraldehyde cross-linked G, PG, EG, and P/EG gels; the 0.01% glutaraldehyde cross-linked G, PG, and EG gels; the 0.001% glutaraldehyde cross-linked G and PG gels; and the self-cross linked LN$_2$-baked G. Swelling study results for P/EG hydrogels and in vitro and in vivo drug release studies are ongoing and results are not included here.

For in vitro drug release studies, each hydrogel was loaded with chlorhexidine digluconate (CHD; Sigma, 20% (w/v) aqueous solution) using the same drug loading density used for dexamethasone in the in vivo studies (150 μg/kg/day, dosage of 21 d). Assuming a rat weight of 0.2 kg, this loading density is equivalent to 630 μg/hydrogel. Based on the maximum swelling weight ratios from the swelling studies, each hydrogel was loaded with 35 μL of CHD (18 mg/ml), a volume well below the maximum volume the hydrogel could absorb. Hydrogels (0.5×0.5×0.6 cm) were placed into individual wells in a 48-well tissue culture plate. CHD was added to each well, and the hydrogels were allowed to absorb the drug solution overnight (approximately 15 hours) with gentle shaking.

To evaluate swelling and degradation kinetics, dried hydrogels were placed in 5 ml of aqueous solutions of pH 4.5, pH 7.0 or pH 7.4 in a water bath at 37° C. Aqueous solutions were created by adjusting the pH of H$_2$O with dilute HCl and NaOH. Hydrogels were transferred to fresh aqueous solutions at approximately 3 and 6 wks. Swollen hydrogels were weighed at 2, 4, and 6 hours, 1, 2, 3, 4, and 5 days, and 1, 2, 3, 4, 5, 6, 7, and 8 weeks to characterize the swelling/degradation kinetics. Extreme care was taken to preserve the integrity of the hydrogels at every step in the weighing process. The swelling weight ratio at each time point for each hydrogel was calculated as: $(W_s - W_d)/W_d$, where $W_s$ is the weight of the swollen gel and $W_d$ is the weight of the dry gel (in grams). The maximum swelling weight ratio that occurred over 8 weeks and the time it occurred was also calculated ($R_{max}$ & $T_{max}$, respectively). The last attainable swelling weight ratio (due to hydrogel dissolution) and the time it occurred was also calculated ($R_{fail}$ & $T_{fail}$, respectively). Statistical analysis was performed using ANOVA and Tukey multiple comparisons tests (p<0.05). Individual sample solutions from the swelling study were collected for ongoing GPC analysis of degradation products (results not shown) (20% (v/v) acetonitrile: 0.1 M NaNO$_3$ at a flow rate of 0.7 ml/min, 60 min., using three Ultrahydrogel columns in series, Ultrahydrogel 250, 1000 and Linear, on a Waters system).

For in vivo studies, unmodified gelatin cross-linked in 0.1% and 0.01% gluteraldehyde were tested in vivo, following the established cage implant system. See Kao & Anderson (1999) "Handbook of Biomaterials Evaluation 2$^{nd}$ ed., Taylor & Frances Publishing, Philadelphia, Pa., pp. 659-671. Samples were placed inside a cylindrical cage (3.5 cm long×1 cm diameter) constructed from medical grade stainless steel wire mesh. Empty cages were implanted as controls. All cages were implanted subcutaneously in the back of 3-month-old female Sprague-Dawley rats. At 4, 7, 14 and 21 days post-implantation, the inflammatory exudates that collected in the cages were withdrawn and analyzed for the quantitative evaluation of cellular and humoral response to implantation using standard hematology techniques. The distributions of lymphocyte, monocyte, and polymorphonuclear leukocyte (PMN) subpopulations in the exudates were determined. Concurrently, the implanted materials were retrieved for analysis of changes in the sample physiochemical composition (e.g., percent mass loss).

Percent modification of the lysyl residues in gelatin by PEG and/or EDTAD was quantified using the TNBS method: The PG was found to be 10% modified, the EG 40% modified, and the P/EG 60% modified. All results reported here incorporate materials from the same batch of modified gelatin (i.e. 8% PG, 42% EG).

Figure 5:
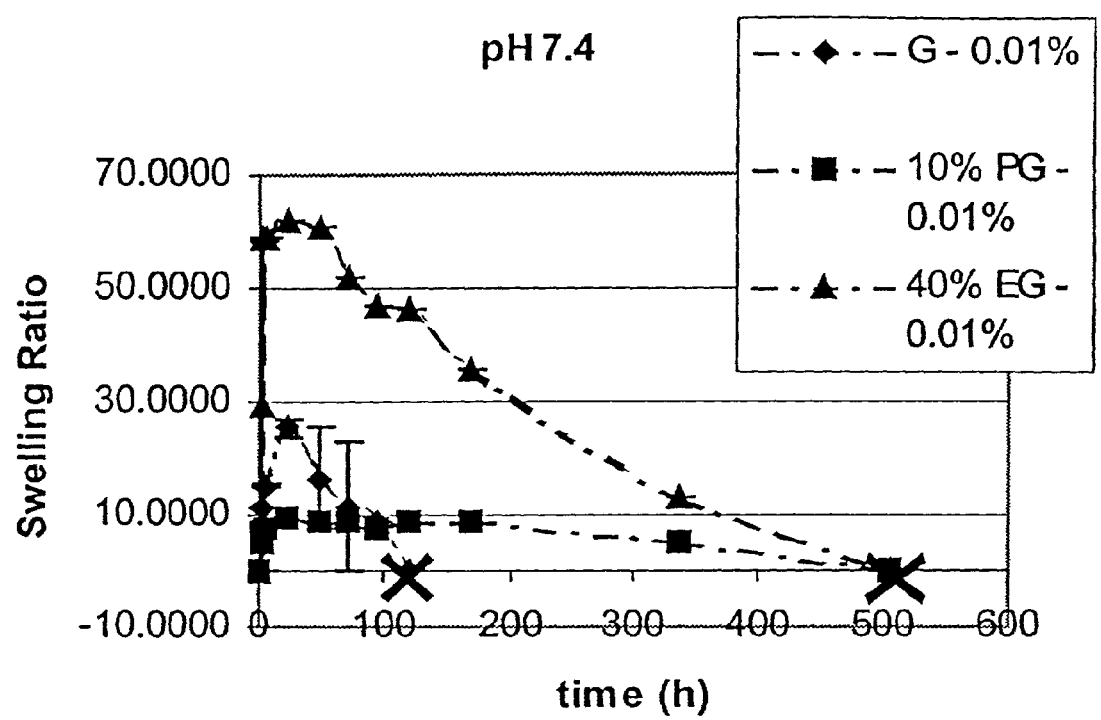
FIG. 5. Graph depicting representative swelling/degradation kinetics. Time in hours is shown on the X-axis; swelling ratio is shown on the Y-axis. Key: G, 0.01% glutaraldehyde cross-linked=♦; 10% PG, 0.01% glutaraldehyde cross-linked=■; 40% EG, 0.01% glutaraldehyde cross-linked=▲.

FIG. 5 is a graph depicting representative swelling/degradation kinetics. Time in hours is shown on the X-axis; swelling ratio is shown on the Y-axis. Key: G, 0.01% glutaraldehyde cross-linked=♦; 10% PG, 0.01% glutaraldehyde cross-linked=■; 40% EG, 0.01% glutaraldehyde cross-linked=▲. Swelling/degradation studies showed that G modified with PEG significantly increased $T_{max}$ and $T_{fail}$, whereas G modified with EDTAD significantly increased $T_{max}$. Hydrogels cross-linked in 0.01% or 0.001% gluteraldehyde showed a significant difference in $T_{max}$ and $T_{fail}$ over gels cross-linked in 0.1% gluteraldehyde. The level of pH did not significantly affect $R_{max}$, $T_{max}$, $R_{fail}$ and $T_{fail}$. Table 5 shows $R_{max}$, $T_{max}$, $R_{fail}$ and $T_{fail}$ for all levels of gluteraldehyde concentration, pH and gelatin backbone modification.

TABLE 5

$R_{MAX}$, $T_{MAX}$, $R_{FAIL}$, AND $T_{FAIL}$ FOR ALL LEVELS OF GLUTERALDEHYDE/HEAT TREATMENT, PH AND GELATIN BACKBONE MODIFICATION

| % gluteraldehyde fixation/heat treatment | pH | G Mod[c] | R-max | T-max | R-fail | T-fail |
|---|---|---|---|---|---|---|
| 0.1% | 4.5 | G | 6.30 | 108 | 4.11 | >1344 |
| | | PG | 6.98 | 1344[b] | 6.98 | >1344 |
| | | EG | 8.77 | 720 | 7.71 | >1344 |
| | 7.0 | G | 5.94 | 108 | 2.88 | >1344 |
| | | PG | 6.64 | 1092 | 4.55 | >1344 |
| | | EG | 12.04 | 1008 | 6.24 | >1344 |
| | 7.4 | G | 4.68 | 96 | 1.45 | 1092 |
| | | PG | 6.60 | 1092 | 5.35 | >1344 |
| | | EG | 894.17 | 924 | 892.52 | >1344 |

TABLE 5-continued $R_{MAX}$, $T_{MAX}$, $R_{FAIL}$, AND $T_{FAIL}$ FOR ALL LEVELS OF GLUTERALDEHYDE/HEAT TREATMENT, PH AND GELATIN BACKBONE MODIFICATION

| % gluteraldehyde fixation/heat treatment | pH | G Mod[c] | R-max | T-max | R-fail | T-fail |
|---|---|---|---|---|---|---|
| 0.01% | 4.5 | G | 35.48 | 36 | 7.25 | 132 |
| | | PG | 11.54[b] | 24 | 5.80 | 420 |
| | | EG | 31.53 | 2 | 14.07 | 84 |
| | 7.0 | G | 40.23 | 48 | 8.49 | 84 |
| | | PG | 10.63 | 96 | 8.36 | 336 |
| | | EG | 26.96 | 2 | 7.71 | 168 |
| | 7.4 | G | 26.29 | 36 | 8.21 | 72 |
| | | PG | 10.48 | 96 | 5.06 | 336 |
| | | EG | 30.88 | 12 | 6.47 | 168 |

TABLE 5-continued $R_{MAX}$, $T_{MAX}$, $R_{FAIL}$, AND $T_{FAIL}$ FOR ALL LEVELS OF GLUTERALDEHYDE/HEAT TREATMENT, PH AND GELATIN BACKBONE MODIFICATION

| % gluteraldehyde fixation/heat treatment | pH | G Mod[c] | R-max | T-max | R-fail | T-fail |
|---|---|---|---|---|---|---|
| 0.001% | 4.5 | G | 0.10 | 1 | −0.01 | 2 |
| | | PG | 0 | 0 | 0 | 0 |
| | | EG | — | — | — | — |
| | 7.0 | G | 0.33 | 1 | 0.17 | 2 |
| | | PG | 0 | 0 | 0 | 0 |
| | | EG | — | — | — | — |
| | 7.4 | G | 0.36 | 1 | 0.36 | 1 |
| | | PG | 0 | 0 | 0 | 0 |
| | | EG | — | — | — | — |
| LN$_2$-baked G | 4.5 | G | 3.96 | 24 | 2.06 | 252[b] |
| | 7.0 | G | 4.76 | 24 | 0.40 | 72 |
| | 7.4 | G | 4.05 | 15 | 72 | 96 |

[a]All values expressed in mean (n = 2 – 3) with s.e.m. omitted for clarity.
[b]Significantly different from G under same experimental conditions; paired t-tests, p < 0.05.
[c]10% PG or 40% EG In vivo studies following the cage implant system allowed the duration and magnitude of the host foreign body reaction to the implanted gelatin-based hydrogels (0.1% G and 0.01% G) to be evaluated. The presence of a high concentration (relative to control) of polymorphonuclear leukocytes (PMNs) in the exudates indicates an acute inflammatory response, which occurs at the onset of implantation and attenuates with time. The presence of a high concentration (relative in control) of monocytes and lymphocytes in the exudates is indicative of the chronic inflammatory response. Thus, 0.1% G hydrogels elicited a slightly enhanced chronic inflammatory response at 7 days and an enhanced chronic inflammatory response at 14 days vs. the control and that of 0.01% G. 0.01% G elicited a slightly enhanced chronic inflammatory response at 7 days vs. the control (see Table 6). By day 21, all samples showed a comparable level of chronic inflammation vs. the controls the proceeded toward resolution. Percent mass loss of samples increased with increasing implantation time and was further increased with decreasing percentage of gluteraldehyde fixation (results not shown).

TABLE 6

TOTAL AND DIFFERENTIAL LEUCOCYTE CONCENTRATION IN THE INFLAMMATORY EXUDATES OF GELATIN HYDROGELS CROSS-LINKED IN 0.1 OR 0.01% GLUTERALDEHYDE

| Sample | Implantation time (day) | Cell concentration (×cells/μL)[a] | | | |
|---|---|---|---|---|---|
| | | Total | Lymphocyte | Monocyte | PMN |
| Empty cage (no sample) | 4 | 184 ± 25 | 168 ± 23 | 16 ± 7 | 1 ± 1 |
| | 7 | 57 ± 12[c] | 49 ± 10[c] | 7 ± 2 | 0 ± 0 |
| | 14 | 55 ± 7 | 36 ± 3 | 12 ± 4 | 7 ± 5 |
| | 21 | 91 ± 69 | 98 ± 54 | 20 ± 16 | 0 ± 0 |
| 0.1% | 4 | 597 ± 392 | 255 ± 116 | 126 ± 113 | 217 ± 212 |
| | 7 | 183 ± 129 | 78 ± 40 | 26 ± 14 | 79 ± 74[b] |
| | 14 | 235 ± 65[b] | 118 ± 30[b] | 40 ± 16 | 77 ± 75 |
| | 21 | 200 | 167 | 33 | 0 |
| 0.01% | 4 | 477 ± 195 | 412 ± 172 | 57 ± 28 | 8 ± 5 |
| | 7 | 178 ± 78[b] | 157 ± 80 | 17 ± 1[b] | 4 ± 3 |
| | 14 | 72 ± 36 | 60 ± 29 | 10 ± 7 | 2 ± 1 |
| | 21 | 93 ± 3 | 72 ± 5 | 9 ± 4 | 12 ± 11 |

[a]All values expressed in mean ± s.e.m. (n = 3 – 7).
[b]Represents p < 0.01 vs. respective values of "empty cage" controls.
[c]Represents p < 0.01 vs. respective values at day 4 of the same sample type.

This Example shows that gelatin backbone modifications and cross-linking agent selection affect the swelling/degradative kinetics of modified gelatin-based hydrogels. By modulating these material properties and monitoring how these changes affect drug release kinetics, a nonimmunogenic, bioresorbable cell/drug carrier matrix can be made that will have desirable release characteristics based on such considerations as the drug being used in the formulation, the length of the treatment, and the condition being treated, and the location of the implanted matrix.

Example 3

In Vivo Modulation of Host Response Using Gels Grafted with Fibronectin-Derived Biomimetic Oligopeptides The host inflammatory reaction is a normal response to injury and the presence of foreign objects. The magnitude and duration of the inflammatory process have a direct impact on biomaterial biostability and biocompatability. Thus, this Example investigates the performance of gels fabricated according to the present invention that include fibronectin-derived biomimetic oligopeptides. Fibronectin in known to adsorb on a variety of biomaterials and play an important role in the host-foreign body reaction. The RGD (SEQ. ID. NO: 1) and PHSRN (SEQ. ID. NO: 2) amino acid sequences are particularly interesting because these sequences are present on adjacent loops of two connecting FIII modules and bind synergistically to a host of integrins.

Oligopeptides were designed based on the primary and tertiary structure of human plasma fibronectin to study the structure-functional relationship of RGD and PHSRN regions of fibronectin in regulating the host inflammatory response and macrophage behavior in vivo. Peptides included RGD and PHSRN sequences alone or in combination. The tertiary structure of fibronectin was utilized as a guide in the formulation of peptides. The distance between the PHSRN sequence and the RGD sequence within the natural fibronectin molecule in solution was approximated using the structural coordinates archived in the SwissProt Database® (sequence FINC_HUMAN P02751). Based on the measurement, a hexamer of glycine ($G_6$) of approximately the same length was used to link the two bioactive sequences in both possible orientations. A terminal trimeric glycine domain ($G_3$) was employed as a spacer in all peptides. Oligopeptides were synthesized using solid-resin methods on an automated peptide synthesizer (Millipore) using conventional 9-fluorenylmethyloxycarbonyl chemistry without further purification and with a final coupling efficiency of approximately ≧85% purity. Peptides were characterized and analyzed using mass spectroscopy and reverse phase HPLC coupled to photodiode array, evaporative light scatter, and UV/Vis detectors. The following oligopeptides were synthesized: $G_3$RGDG (SEQ. ID. NO: 3), $G_3$PHSRNG (SEQ. ID. NO: 4), $G_3$RGDG$_6$PHSRNG (SEQ. ID. NO: 5), $G_3$PHSRNG$_6$RGDG (SEQ. ID. NO: 6), and $G_3$RDGG (SEQ. ID. NO: 7) as a nonspecific control. Peptides were covalently grafted onto hydrogels as described in Example 1 to investigate the influence of peptides on the host response and macrophage behavior in vivo.

The gels used in this Example were random co-polymers of monomethoxy polyethyeneglycol monoacrylate (mPEGmA), acrylic acid (Ac), trimethylolpropane triacrylate (TMPTA). As noted above, these gels are hydrophilic, nonionic, low swelling, glassy, optically transparent, and colorless. Differential scanning calorimetry analysis showed that these materials are completely amorphous and the mPEGmA component is completely phase-mixed in the cross-linked TMPTA matrix. The bioactive oligopeptides were grafted onto mPEGmA-co-Ac-co-TMPTA hydrogels and the resulting gels mediated cell adhesion in a receptor-peptide specific manner. The peptide surface density was found to be dependent on the number of amino acids per peptide. For example pentapeptides were grafted at 66±6 pmol/cm$^2$ surface density; whereas, peptides containing 30 residues were grafted at approximately one-fifth of that surface density. In this Example, oligopeptides containing one bioreactive region (i.e., $G_3$RGDG, G3PHSRNG, and $G_3$RDGG) were grafted at about twice the density of oligopeptides containing two bioreactive regions (i.e., $G_3$RGDG$_6$PHSRNG and $G_3$PHSRNG$_6$RGDG).

The well-established subcutaneous cage-implant system was utilized to study the effect of implanted materials on the host foreign body reaction. Briefly, mPEGmA-co-Ac-co-TMPTA networks grafted with or without fibronectin-derived peptides were placed in sterile water for at least 48 hours to remove low molecular weight leachable residual molecules from the polymerization process and to achieve hydration equilibrium. The polymer samples were then inserted under sterile conditions into an autoclaved cylindrical cage measured 3.5 cm long, 1 cm in diameter, and constructed from medical grade stainless steel wire mesh. Cages containing various polymer samples were subcutaneously implanted at the back of 3-month old female Sprague-Dawley rats. Empty cages were employed and implanted as controls. The inflammatory exudate that collects in the cage was withdrawn at 4, 7, 10, 14, and 21 days post-implantation and analyzed for the quantitative evaluation of cellular and humoral response to the test material using standard and conventional hematology techniques. Specifically, the distribution of lymphocyte, monocyte, and PMN subpopulations in the exudate was determined. The presence of a high concentration of PMNs in the inflammatory exudate indicates an acute inflammatory response, which occurs from the onset of implantation and attenuates with time. This is followed by the chronic inflammatory response, which is characterized by the presence of a high concentration of monocytes and lymphocytes in the exudate. Hence, the cage implant system allows the host inflammatory reaction to the test sample to be observed as a function of time and material property. A drop of each exudate sample was also cultured on brain-heart infusion agar plates to check for incidence of infection. No infection was observed at any retrieval time for any sample. At 4, 7, 14, 21, 35, and 70 days post-implantation, test polymer samples were retrieved and the adherent cell morphology and density were quantified using a video analysis system coupled to a light microscope.

A previously developed mathematical model describing the in vivo kinetics of macrophage fusion on various biomaterials was employed to provide insights into the effect of materials and peptides on foreign body giant cell (FBGC) formation. The model was formulated based on Flory's most-probable molecular weight distribution of polymer chains. In the analysis, each adherent macrophage is analogous to a monomer and the process of cell fusion is analogous to the polymerization process. Two initial premises are necessary: (1) the FBGC size is directly proportional to the number of nuclei in a given FBGC; and (2) the ability for each cell to fuse is constant and independent of the cell size. The FBGC size-distribution equation ($N_x = p^{ax-3}(1-p)$) was applied to the measured FBGC size-distribution result of each sample at each retrieval time. $N_x$ is the cell size number-fraction of FBGCs with area x; p is the probability of cell fusion or the ratio of the number of cell fusion to the initial adherent macrophage density; a is a constant relating to the number of nuclei per FBGC to the cell area (FBGC/mm$^2$) and has been found to be constant for various clinically relevant biomaterials under different mechanical stress conditions. See Kao et al. (1994) *J. Biomed. Mater. Res.* 28:73-79; Kao et al. (1995) *J. Biomed. Mater. Res.* 29(10); 1267-75; and Kao et al. (1994) *J. Biomed. Mater. Res.* 2:819:829. Values for p and a were obtained through a curve-fit iteration until r$^2$>0.98. The resulting values of p for each sample at each retrieval time were utilized to calculate two kinetic parameters that characterize the process of cell fusion: the density of adherent macrophages that participate in the FBGC formation ($d_0 = d/[p^2(1-p)]$) and the rate constant of cell fusion ($1/(1-p) = d_0 tk + 1$). $d_0$ is the calculated density of adherent macrophages that participate in the FBGC formation process (macrophages/mm$^2$), $d_f$ the measured adherent macrophage density at 4 days post-implantation (macrophages$^1$mm$^{-2}$), t the implantation time (week), and k the inverse rate constant of cell fusion (mm$^2$cell$^{-1}$ week$^{-1}$).

All experimental results are expressed in mean±standard error of the mean. Each sample was independently repeated 3 times (n=3). Comparative analyses were performed with Statview® 4.5 using analysis of variance and Fisher's protective t-test at 95% confidence level (p<0.05).

Total and differential leukocyte analysis was performed at several post-implantation periods (Table 7). No PMNs were observed at any time point for all samples, indicating that the presence of empty cages and networks grafted with or without fibronectin-derived biomimetic oligopeptides elicited a rapid acute inflammatory response that was resolved within 4 days of implantation. For the empty cage control, total leukocyte and lymphocyte concentrations decreased rapidly between 4 and 7 days post-implantation and remained steady thereafter up to 21 days. Monocyte concentration remained constant from 4 to 21 days post-implantation. These results indicate that the presence of the empty cage elicited a rapidly decreasing chronic inflammatory response by 7 days post-implantation that turned toward resolution with increasing implantation time. The presence of mPEGmA-co-Ac-co-TMPTA gels within the cage showed a constant total leukocyte concentration from 4 to 21 days of implantation. However, the presence of the gels increased monocyte concentration and lowered lymphocyte concentration at days 4 and 7 when compared with that of empty cage controls, suggesting a comparable level of chronic inflammatory response that turned toward resolution but with an altered leukocyte sob-population distribution. When comparing the trends between mPEGmA-co-AC-co-TMPTA networks and empty cage controls, the presence of immobilized peptides on the polymer network did not significantly affect the total and differential leukocyte concentrations up to 14 days post-implantation, except that the decreased lymphocyte concentration was not observed for $G_3$RGDG-grafted networks at days 4 and 7 and for other peptide-grafted surfaces at day 7 of implantation.

These results indicate that the presence of polymer networks with or without immobilized peptides did not significantly modify the host acute and chronic inflammatory reactions up to 14 days of implantation. By 21 days of implantation, the presence of grafted $G_3$RGDG or $G_3$RDGG slightly decreased the total and lymphocyte concentrations when compared with respective values of "no grafted peptides" and "empty cage" controls. This trend was not observed for surfaces grafted with $G_3$PHSRNG$_6$RGDG. Conversely, the presence of grafted $G_3$PHSRNG or $G_3$RGDG$_6$PHSRNG slightly increased the total and lymphocyte concentrations when compared with respective values of "no grafted peptides" controls (p<0.05). At 21 days post-implantation and thereafter, extensive fibrous encapsulation at the exterior of all implanted cages and the absence of the inflammatory exudate inside the cage were observed for all samples, indicating the progression of tissue healing. These data suggest that the identity of grafted peptides did not significantly alter the temporal variation and intensity of the host acute and chronic inflammatory reaction.

Adherent macrophage density on implanted mPEGmA-co-AC-co-TMPTA networks grafted with or without fibronectin-derived oligopeptides was quantified at different retrieval times. In general, adherent macrophages on all surfaces decreased with increasing implantation time (see Table 8). Adherent macrophage densities for all samples were comparable and were higher than respective values of $G_3$RDGG or "no grafted peptide" controls at each retrieval time up to 14 days post-implantation. Adherent macrophage density on all samples was comparable from 21 to 70 days post-implantation. Adherent macrophages on all surfaces showed an extensive spread morphology with pseudopodial extension. These results indicate that peptides containing RGD and/or PHSRN motifs do not affect adherent macrophage density.

At each retrieval time up to 70 days post-implantation, no surface cracking, pitting, nor other evidence of physical degradation were observed under polarized light microscope at 40× magnification on any polymer sample with or without grafted peptides.

The morphology of FBGCs on all samples was that of foreign-body type, i.e., random arrangements of nuclei numbered more than three nuclei per cell with widely variable, extensive cytoplasmic forms. In general, FBGC density increased with increasing implantation time for all samples except that on surfaces grafted with $G_3$RGDG or $G_3$PHSRNG$_6$RGDG at which the adherent FBGC density remained constant with increasing implantation time (data not shown). In addition, the average FBGC size increased with increasing implantation time for all samples (data not shown).

These results showed that hydrogels grafted with fibronectin-derived peptides mediated extensive FBGC coverage that increased with increasing implantation time. Specifically, surfaces grafted with $G_3$RGDG$_6$PHSRNG showed the highest FBGC coverage at about 90% of the total sample area when compared with other sample types and controls at 70 days post-implantation. These in vivo findings indicate that the RGD motif, specifically in the configuration of $G_3$RGDG or $G_3$PHSRNG$_6$RGDG, but not G3RGDG$_6$PHSRNG, modulates a rapid macrophage fusion to form FBGCs. This phenomenon is observed at the early stage of implantation (i.e., within 4 days of implantation).

A previously developed mathematical model describing the in vivo kinetics of macrophage fusion to form FBGCs on biomaterials was employed to provide insights into the effect of peptide identity on the kinetics of FBGC formation. FBGC cell size distributions on all samples were measured at 4, 7, 14, and 21 days post-implantation. The FBGC cell size-distribution equation was fitted to the measured results of each sample at each retrieval time to obtain values for p and 1/a. Values for p increased with increasing implantation time for all samples except for that of the "no grafted peptide" controls. Thus, these results indicate that the probability of cell fusion increased with increasing implantation time. The calculations also showed that the density of adherent macrophages that participate in the FBGC formation was significantly higher for mPEGmA-co-Ac-co-TMPTA gels grafted with $G_3$RGDG, $G_3$PHSRNG, and $G_3$PHSRNG$_6$RGDG than that for gels grafted with $G_3$RDGG nonspecific controls and gels without peptide grafting.

This Example shows that the hydrogels of the present invention can be used to support peptide, proteins, and the like, within a modified, three-dimensional hydrogel matrix.

TABLE 7

Total and different leukocyte concentration in the inflammatory exudate of mPEGmA-co-AC-co-TMPTA networks grafted with various fibronectin-derived oligopeptides[a]

| Peptide | Implantation (days) | Cell concentration (×10 cells/μl) | | | |
|---|---|---|---|---|---|
| | | Total | Lymphocyte | Monocyte | PMN |
| G$_3$RGDG | 4 | 127 ± 25 | 71 ± 22 | 56 ± 5[b] | 0 ± 0 |
| | 7 | 67 ± 13 | 24 ± 4[c] | 43 ± 9[b] | 0 ± 0 |
| | 14 | 74 ± 18 | 21 ± 4 | 53 ± 25 | 0 ± 0 |
| | 21 | 31 ± 8[c,d,b] | 27 ± 8[c,b] | 5 ± 1[d] | 0 ± 0 |
| G$_3$PHSRNG | 4 | 63 ± 32 | 25 ± 22[b] | 38 ± 17[b] | 0 ± 0 |
| | 7 | 61 ± 9 | 25 ± 6 | 36 ± 3[b] | 0 ± 0 |
| | 14 | 56 ± 19 | 33 ± 15 | 24 ± 4 | 0 ± 0 |
| | 21 | 77 ± 2[c] | 69 ± 2[c,d] | 7 ± 3 | 0 ± 0 |
| G$_3$RGDG$_6$PHSRNG | 4 | 129 ± 52 | 29 ± 10[b] | 99 ± 62[b] | 1 ± 1 |
| | 7 | 68 ± 23 | 24 ± 6 | 44 ± 17[b] | 0 ± 0 |
| | 14 | 57 ± 12 | 21 ± 9 | 36 ± 10 | 0 ± 0 |
| | 21 | 74 ± 2[c] | 67 ± 3[c,d] | 7 ± 3 | 0 ± 0 |
| G$_3$PHSRNG$_6$RGDG | 4 | 109 ± 16 | 53 ± 14[b] | 56 ± 5[b] | 0 ± 0 |
| | 7 | 49 ± 11[d] | 21 ± 8 | 28 ± 3[b,d] | 0 ± 0 |
| | 14 | 87 ± 23 | 38 ± 12 | 49 ± 29 | 0 ± 0 |
| | 21 | 60 ± 11 | 55 ± 8 | 5 ± 3[d] | 0 ± 0 |
| G$_3$RDGG | 4 | 91 ± 11 | 51 ± 1[b] | 40 ± 10[b] | 0 ± 0 |
| | 7 | 66 ± 16 | 30 ± 11 | 36 ± 6[b] | 0 ± 0 |
| | 14 | 48 ± 9[d] | 23 ± 6[d] | 25 ± 6 | 0 ± 0 |
| | 21 | 35 ± 10[c,d,b] | 32 ± 9[c,b] | 4 ± 2[d] | 0 ± 0 |
| No grafted peptide | 4 | 94 ± 32 | 42 ± 27[b] | 52 ± 16[b] | 0 ± 0 |
| | 7 | 41 ± 10 | 11 ± 2[b] | 30 ± 6[b] | 0 ± 0 |
| | 14 | 89 ± 21 | 56 ± 18 | 33 ± 15 | 0 ± 0 |
| | 21 | 63 ± 4 | 55 ± 4 | 7 ± 2[d] | 0 ± 0 |
| Empty cage | 4 | 135 ± 22 | 129 ± 22 | 6 ± 1 | 0 ± 0 |
| | 7 | 42 ± 8[d] | 38 ± 8[d] | 4 ± 1 | 0 ± 0 |
| | 14 | 51 ± 10[d] | 35 ± 6[d] | 15 ± 10 | 0 ± 0 |
| | 21 | 82 ± 22[d] | 80 ± 25[d] | 2 ± 2 | 0 ± 0 |

[a]All values expressed in (mean ± s.e.m. (n = 3).
[b]Represents $p < 0.05$ vs. respective values of "empty cage" controls.
[c]Represents $p < 0.05$ vs. respective values of "no grafted peptide" controls.
[d]Represents $p < 0.05$ vs. respective values at day 4 of the same sample type.

TABLE 8

Adherent macrophage density on cage-implanted mPEGmA-co-AC-co-TMPTA networks grafted with various fibronectin-derived oligopeptides[a]

| Peptide | Adherent macrophage density (×10 macrophages/mm$^2$) at various post-implantation time (days) | | | | | |
|---|---|---|---|---|---|---|
| | 4 | 7 | 14 | 21 | 35 | 70 |
| G$_3$RGDG | 138 ± 22[b] | 85 ± 12[b,c] | 33 ± 12[b,c] | 15 ± 3[c] | 14 ± 2[c] | 4 ± 2[c] |
| G$_3$PHSRNG | 124 ± 12[b] | 57 ± 10[b,c] | 31 ± 11[b,c] | 10 ± 0[c] | 9 ± 1[c] | 4 ± 2[c] |
| G$_3$EGDG$_6$PHSRNG | 126 ± 8[b] | 58 ± 12[b,c] | 23 ± 4[b,c] | 14 ± 4[c] | 6 ± 5[c] | 0 ± 0[c] |
| G$_3$PHSRNG$_6$RGDG | 183 ± 27[b] | 69 ± 6[b,c] | 30 ± 5[b,c] | 16 ± 4[c] | 12 ± 5[c] | 3 ± 1[c] |
| G$_3$RDGG | 75 ± 16 | 36 ± 5[c] | 15 ± 3[c] | 15 ± 6[c] | 9 ± 3[c] | 3 ± 2[c] |
| No grafted peptide | 74 ± 26 | 37 ± 4[c] | 14 ± 2[c] | 19 ± 3[c] | 6 ± 3[c] | 1 ± 1[c] |

[a]All values expressed in mean ± s.e.m. (n = 3).
[b]Represents $p < 0.05$ vs. respective values of "no grafted peptide" controls.
[c]Represents $p < 0.05$ vs. respective values at day 4 of the same sample type.

Example 4

Interpenetrating Membranes Comprising Modified Hydrogels

Interpenetrating networks (IPNs) are hydrogels synthesized by reacting a first polymer around a second material to form an intermeshing structure. IPNs are free of cross-linkers used to create other biomedical hydrogels. In addition to the benefit of being free of potentially toxic chemicals used in conventional cross-linking procedures, photopolymerization has the advantages that the desired amount of drug can be easily loaded into the matrix, and the cross-linking density, which can affect the drug release rate, can be controlled. Furthermore, IPNs can be formed in situ and used in places less suitable for prefabricated materials.

The focus of this Example was to investigate the swelling and drug release kinetics of gelatin-based IPNs of varying gelating backbone modification, weight percent of gelatin, pH, and the molecular weight of polyethylene glycol diacrylate (PEGdA). Based on our results, these IPNs are quite suitable for tissue scaffolds and drug release vehicles.

Polyethyleneglycol (PEG) (Aldrich; 2, 4.6, and 8 kDa) was modified with acrylolyl chloride (Aldrich) and TEA (Aldrich) in a 1:4:6 molar ratio at room temperature for 3 hours to produce polyethylene glycol diacrylate (PEGdA). The final PEGdA product purity was checked with the same reverse phase HPLC system as used in Example 1. The elution time of the PEGdA was approximately 13.2 minutes with a purity of approximately 100 wt % PEGdA.

Monomethoxypolyethyleneglycol (mPEG) (Fluka; 2 kDa) was modified with acetic anhydride (Aldrich) and DMSO (Fisher) in a 1:80:140 molar ratio at room temperature to form an mPEG monoaldehyde (mPmA). The reaction takes 8 to 24 hours and was monitored periodically with HPLC. The mPmA had an elution time of approximately 11.9 minutes and a purity close to 75 wt % mPmA. The compositions of PEGdA and mPEGmonoaldehyde were also confirmed with $^1$H-NMR.

Figure 4:
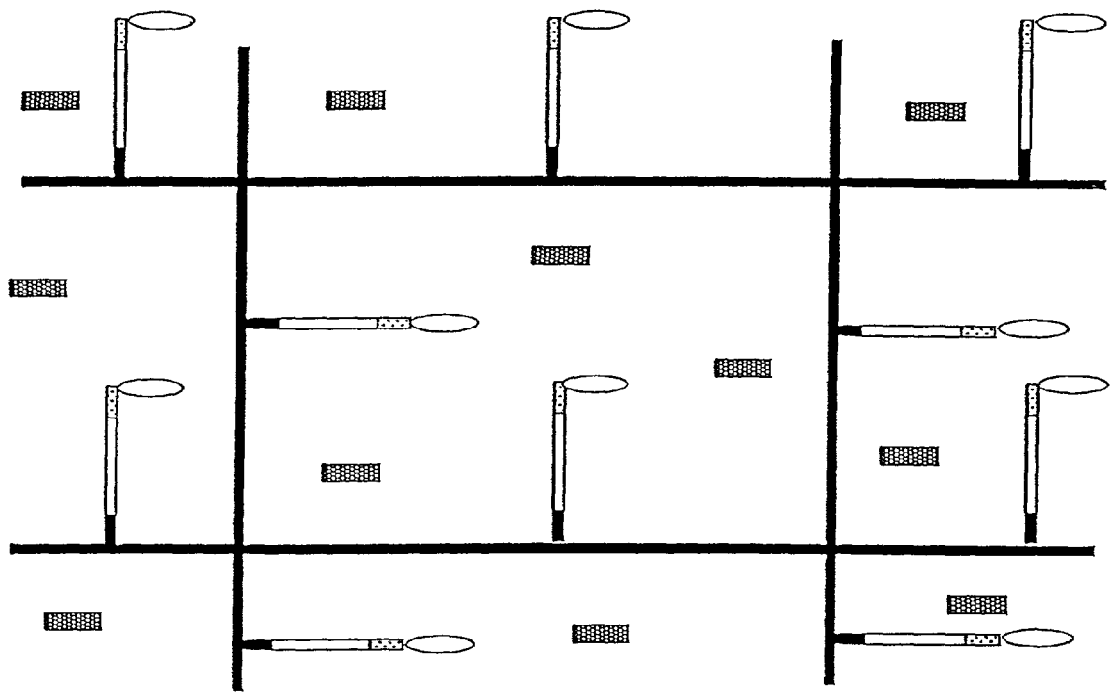
FIG. 4. A schematic representation of hydrogels according to the present invention.

Gelatin (G) (Sigma, Type A: from porcine skin, 300 bloom) lysyl groups were modified with EDTAD in a 1:0.034 weight ratio for 3 hours at pH=10 to form EDTAD-G (EG). Gelatin lysyl groups were also modified with mPmA and sodium cyanoborohydride (NaCNBH$_3$) (Aldrich) in a 1:0.66:0.186 weight ratio for 24 hours at 50 to 60° C. to form mPmAG (FIG. 4). EG was further modified with mPmA in a procedure similar to the mPmAG procedure. The percent of the gelatin lysyl residues modified by EDTAD and/or mPmA was determined using the trinitrobenzene sulfonic acid spectrophotometric method. The IPNs used in this study were prepared from the same modified gelatins.

IPNs were created using modified and unmodified gelatin, PEGdA (2, 4.6, or 8 kDa molecular weight), initiator (2,2-dimethoxy-2-phenylacetophenone, DMPA), and a long wavelength UV source. Gelatin was dissolved in deionized water with heat (80° C.) to form a 20 wt % gelatin solution. PEGdA was dissolved in deionized water, without heat, in an aluminum foil wrapped glass vial to form a 100 wt % PEGdA solution. The gelatin solution was then added to the PEGdA solution and the mixture was agitated thoroughly. DMPA was then added to the gelatin/PEGdA mixture and this final mixture was again agitated and then heated (80° C.) throughout the rest of the procedure. IPNs were created through injection molding. The final gelatin/PEGdA/DMPA mixture was injected with a Pasteur pipette into a Teflon mold that was clamped between 2 glass slides. The mold has the approximate dimensions of 20 mm long by 10 mm wide by 1.6 mm thick. The mold/IPN mixture was then irradiated with UV light from the top and bottom for approximately 3 minutes. During this time, the UV light initiates the cross-linking of PEGdA, entrapping the gelatin within the PEGdA cross-links. The mold/IPN was allowed to cool before the IPN was removed from the mold.

IPNs were named based on the weight percent of gelatin, the type of gelatin, the weight percent of PEGdA, and the molecular weight of the PEGdA used to synthesize the IPN. For example, 4G6P2k indicates 40 wt % gelatin, 60 wt % PEGdA, 2 kDa PEGdA. The following key describes the code used to identify IPN formulations.

Key: Each formulation is identified by a code of the formula "XYZk", where X is the wt % gelatin, Y is the type of gelatin, Z is the wt % PEGdA, and k is the molecular weight of the PEGdA:

X=wt % gelatin
4=40 wt %
6=60 wt %
Y=type of gelatin
G=gelatin
EG=EDTAD-modified gelatin
mPMaG=mPmA-modified gelatin
mPmAEG=mPmA/EDTAD-modified gelatin
Z=wt % PEGdA
4=40 wt %
6=60 wt %
k=molecular weight PEGdA
2k=2000 Da
4.6 k=4,600 Da
8k=8,000 Da The swelling/degradation kinetics of the IPNs were characterized by weighing swollen IPNs at predetermined times (up to 8 weeks). The IPNs were added to test tubes containing 5 ml deionized water with environmental pHs of 4.5, 7.0, and 7.4. The test tubes were then placed in water baths at 37° C. At the predetermined times, the samples were removed with extreme caution from the test tubes using a bent spatula, blotted dry, weighed, and then placed back in the same test tube. This was done until the sample had degraded completely or until the sample had degraded into too many pieces and they could no longer be removed from the test tube. The swelling weight ratio at each time point for each IPN was calculated as: $(W_s-W_o/W_o)$, where $W_s$ is the weight of the swollen IPN and $W_o$ is the original weight of the IPN. The maximum swelling weight ratio that occurred over 8 weeks and the time it occurred was calculated ($R_{max}$, $T_{max}$). The last attainable swelling weight ratio (due to IPN degradation) and the time it occurred was also calculated ($R_{fail}$, $T_{fail}$).

The level of host biocompatibility and inflammatory reaction of the IPNs was determined via the in vivo subcutaneous cage implant system described in the previous Examples. IPNs were placed inside cylindrical (1 cm diameter by 3.5 cm long) medical grade stainless steel wire mesh cages. These cages along with empty cages, controls, were implanted subcutaneously at the back of 3-month old female Sprague-Dawley rats. Inflammatory exudates that collected in the cages were withdrawn at 4, 7, 14, and 21 days post-implantation and analyzed for the quantitative evaluation of cellular and humoral response to the IPN samples using standard hematology techniques. Using these techniques the distributions of polymorphonuclear leukocyte (PMN), lymphocyte, and monocyte subpopulations in the exudates were determined. In addition to the host response, the degradation of the IPNs was determined as percent weight lost ((final IPN weight/initial IPN weight)×100).

The IPNs fabricated as described hereinabove were opaque, flexible, rubbery, and slightly tacky. The opacity increased with decreasing gelatin concentration and with increasing PEGdA molecular weight. Increasing the gelatin concentration increased the flexibility and the tackiness of the IPN. The flexibility of the IPNs also seemed to increase with increasing PEGdA molecular weight.

The mechanical properties of the IPNs were tested using ASTM testing standards. The IPNs for mechanical testing were made in a similar fashion as stated above, however the molds used were made of polydimethylsiloxane and the IPN final dimensions were 280 mm thick, 11 mm gauge length, and 2 mm neck width (the dimensions required for ASTM D38-98 type IV specimens). The IPNs were subjected to tensile testing per ASTM D638-98 standards, using an Instron Model 5548 testing machine.

The preliminary mechanical tests indicated that the average Young's Modulus of the 4G6P2K IPNs was 1.26±0.14 N/nm$^2$. The ultimate tensile stress and strain were 0.39±0.10 N/nm$^2$ and 0.49±0.07 mm/mm, respectively.

Swelling/degradation studies (Table 9) showed that increasing the molecular weight of the PEGdA to 4.6 kDa and 8 kDa increased the maximum swelling ratio ($R_{max}$). Modifying gelatin with EDTAD and mPmA did not appear to affect $R_{max}$. The time to $R_{max}$ ($T_{max}$) increased with increasing PEGdA molecular weight and by modifying gelatin. The swelling ratio at failure ($R_{fail}$) decreased when the wt % of gelatin was decreased from 60 to 40 when PEGdA molecular weight was held constant at 2 kDa. In addition, when the PEGdA molecular weight was 2 kDa and the gelatin was 60 wt %, modifying the gelatin did not improve $R_{fail}$. The time to reach $R_{fail}$ ($T_{fail}$) was not affected by increasing the molecular weight of PEGdA or by modifying the gelatin. Table 9 shows $R_{max}$, $T_{max}$, $R_{fail}$, and $T_{fail}$ for each composition of IPNs tested at pH=7. These trends were comparable at pH of 4.5 and 7.4 (results not shown). The release kinetics and bioactivity of human serum albumin, chlorhexidine gluconate, and b-FGF (1%) from these IPNs in vitro are currently being quantified.

TABLE 9

Rmax, Tmax, Rfail, and Tfail FOR VARIOUS IPN FORMULATIONS AT pH 7.0

| Formulation | $R_{max}$ | $T_{max}$ | $R_{fail}$ | $T_{fail}$ |
|---|---|---|---|---|
| 6G4P2K | 0 | 0 | −0.736 | 9 |
| 4G6P2K | 0.754 | 1 | <0.444 | >1344 |
| 6G4P4.6K | 1.733 | 225.667 | <0.505 | >1344 |
| 4G6P4.6K | 2.2 | 4.333 | <1.538 | >1344 |
| 6G4P8K | 1.646 | 225 | 0.758 | 451.333 |
| 4G6P8K | 3.911 | 227.333 | <1.542 | >1344 |
| 6EG4P2K | 0.128 | 1 | −0.214 | 336.33 |
| 4EG6P2K | 0.712 | 27 | <0.532 | >1344 |
| 6EG4P4.6K | 2.288 | 35.333 | <0.818 | >1344 |
| 4EG6P4.6K | 1.452 | 17.667 | <0.773 | >1344 |
| 6EG4P8K | 2.639 | 5 | 0.794 | 960 |
| 4EG6P8K | 3.026 | 1 | −0.252 | 1097.3 |
| 6mPmAG4P2K | 0.469 | 1.667 | <−0.23 | >1344 |
| 4mPmAG6P2K | 0.891 | 672 | <0.827 | >1344 |
| 6mPmAG4P4.6K | 2.467 | 226.667 | <0.621 | >1344 |
| 4mPmAG6P4.6K | 2.578 | 616 | <2.445 | >1344 |
| 6mPmAG4P8K | 3.854 | 336.667 | 2.717 | 944 |
| 4mPmAG6P8K | 6.075 | 337 | <2.626 | >1344 |
| 6mPmAEG4P8K | 2.715 | 2.333 | <1.265 | >1344 |
| 4mPmAEG6P8K | 4.224 | 192.333 | <1.472 | >1344 |

40 wt % gelatin, 60 wt % PEGdA 2 kDa (4G6P2K) IPNs were used in a preliminary in vivo study. The presence of a high concentration of PMN in the exudates, relative to the control, indicates an acute inflammation response, due to the onset of implantation, which attentuates with time. Acute inflammation is followed by a high concentration of monocytes and lymphocytes in the exudates, chronic inflammation. The study showed that there was a statistically higher inflammatory response to the IPNs after 4, 7, and 14 days of implantation compared to the empty cage controls. The study also revealed that almost 70% of the sample mass was lost after 4 days, and decreased another 10% after 21 days.

Currently an in vivo study is underway. The study is investigating the drug release and effect of dexamethasone from IPNs of composition 40 wt % gelatin, 60 wt % PEGdA 2 kDa, and 60 wt % PEGdA 2 kDa.

The Example illustrates that IPNs made according to the present invention can serve as tissue scaffolds and drug delivery vehicles.

REFERENCES

1. Y. Inada, M. Furukawa, H. Sasaki, Y. Kodera, M. Hiroto, H. Nishimura, and A. Matsushima, *Trends Biotechnol.* 13:86 (1995).
2. C. Delgado, G. E. Francis, and D. Fisher, *Crit. Rev. Ther. Drug Carrier Syst.* 9:249 (1992).
3. R. Mehvar, *J. Pharm. Pharm. Sci.* 3:125 (2000).
4. G. Fortier, *Biotechnol. Genet. Eng. Rev.* 12:329 (1994).
5. J. M. Harris and S. Zalipsky, "Poly(ethylene glycol) Chemistry and Biological Applications," American Chemical Society, Washington, D.C. (1997).
6. S. Zalipsky and G. Barany, *J. Bioact. Biocompatible Polym.* 5:227 (1990).
7. M. Yokoyama et al., *Bioconjugate Chem.* 3:275 (1992).
8. T. Nakamura, Y. Nagasaki, et al., *Bioconjugate Chem.* 9:300 (1998).
9. Y. Nagasaki et al., *Macromolecules,* 30:6489 (1997).
10. P. D. Drumheller and J. A. Hubbell, *J. Biomed. Mater. Res.* 29:207 (1995).
11. W. J. Kao and J. A. Hubbell JA, *Biotech. Bioengrn.*, 59:2 (1998).
12. W. J. Kao, D. Lee, J. C. Schense, and J. A. Hubbell, *J. Biomed. Mater. Res.* (in press, 2001).
13. W. J. Kao and D. Lee, *Biomaterials* (in press, 2001).
14. R. D. Brown, R. Champion, P. S. Elmes, and P. D. Godfrey. *J. Am. Chem. Soc.,* 107:4109 (1985).
15. The Chemistry of Acrylonitrile. 2d ed. The American Cyanamid Company, New York, N.Y., 17 (1959).
16. H. A. Bruson. *Organic Reactions,* 5:79 (1949).
17. H. Houben-Weyl, E. Muller, and T. Verlag. "Methoden der Organischen Chemie." Stuttgart, XIII, 377 (1970).
18. A. F. Buckmann and M. Morr. *Makromol. Chem.,* 182:1379 (1981).
19. J. M. Harris, J. M. Dust, M. R. Sedaghat-Herati et. al., *Am. Chem. Soc., Polymer Preprints,* 30:356 (1989).
20. J. M. Harris. *Macromol. Chem. Phys.,* C25:325 (1985).

What is claimed is:

1. A method of administering pharmacologically-active agents or cells to a patient in need thereof, the method comprising administering a hydrogel to a patient in need of the pharmacologically-active agent or cells, wherein the pharmacologically-active agent or living cells are entrained within the hydrogel, and the hydrogel comprises:
a first polymer matrix containing reactive amino acid moieties;
a second polymer matrix that interpenetrates with the first polymer matrix;
a bifunctional modifier comprising a compound of formula:

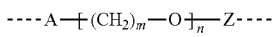

wherein at least one of the "A" or "Z" moieties is covalently bonded to the reactive amino moieties of the polymer matrix; and wherein "A" and "Z" are independently selected from the group consisting of hydrogen, halo, hydroxy, $C_1$-$C_{24}$-alkyl, $C_1$-$C_{24}$-alkenyl, $C_1C_{24}$-alkynyl, $C_1$-$C_{24}$-alkoxy, $C_1$-$C_{24}$-heteroalkyl, $C_1$-$C_{24}$-hetero alkenyl, $C_1$-$C_{24}$-heteroalkynyl, cyano-$C_1$-$C_{24}$-alkyl, $C_3$-$C_{10}$-cycloalkyl, $C_3$-$C_{10}$-cyclo alkenyl, $C_3$-$C_{10}$-cycloalkynyl, $C_3$-$C_{10}$cycloheteroalkyl, $C_3$-$C_{10}$-cycloheteroalkenyl, $C_3$-$C_{10}$-cycloheteroalkynyl, acyl, acyl-$C_1$-$C_{24}$-alkyl, acyl-$C_1$-$C_{24}$-alkenyl, acyl-$C_1$-$C_{24}$-alkenyl, carboxy, $C_1$-$C_{24}$-alkylcarboxy, $C_1$-$C_{24}$-alkenylcarboxy, $C_1$-$C_{24}$-alkynylcarboxy, carboxy-$C_1$-$C_{24}$-alkyl, carboxy-$C_1$-$C_{24}$-alkenyl, carboxy-$C_1$-$C_{24}$-alkynyl, aryl, aryl-$C_1$-$C_{24}$-alkyl, aryl-$C_1$-$C_{24}$-alkenyl, aryl-$C_1$-$C_{24}$-alkynyl, heteroaryl, heteroaryl-$C_1$-$C_{24}$-alkyl, heteroaryl-$C_1$-$C_{24}$-alkenyl, heteroaryl-$C_1$-$C_{24}$-alkynyl, sulfonate, arylsulfonate, and heteroarylsulfonate;
"m" is an integer of from 2 to 8; and
"n" is an integer equal to or greater than 100.

2. The method of claim 1, further comprising a pharmacologically-active agent covalently bonded to one of the "A" or "Z" moieties that is not bonded to the first polymer matrix.

3. The method of claim 1, where the first polymer matrix is proteinaceous.

4. The method of claim 1, wherein the first polymer matrix is selected from the group consisting of gelatin, calcium alginate, calcium/sodium alginate, collagen, oxidized regenerated cellulose, carboxymethylcellulose, amino-modified cellulose, and whey protein.

5. The method of claim 1, wherein the first polymer matrix is selected from the group consisting of gelatin and collagen.

6. The method of claim 1, wherein the first polymer matrix is cross-linked with a cross-linking reagent.

7. The method of claim 1, wherein the first polymer matrix is cross-linked with glutaraldehyde.

8. The method of claim 1, wherein the first polymer matrix further comprises EDTAD moieties bonded to it.

9. The method of claim 1, wherein "n" is equal to or greater than 200.

10. The method of claim 1 wherein "n" is equal to or greater than 2,000.

11. The method of claim 1, wherein "n" is equal to or greater than 20,000.

12. The method of claim 1, wherein the pharmacologically active agent is selected from the group consisting of vulnerary agents, hemostatic agents, antibiotics, antithelmintics, antifungal agents, hormones, anti-inflammatory agents, proteins, polypeptides, oligonucleotides, cytokines, and enzymes.

13. The method of claim 12, wherein the pharmacologically active agent is a vulnerary agent.

14. The method of claim 1, wherein the pharmacologically active agent is selected from the group consisting of vulnerary agents, hemostatic agents, antibiotics, antithelmintics antifungal agents, hormones, anti-inflammatory agents, proteins, polypeptides, oligonucleotides, cytokines, and enzymes.

15. The method of claim 14, wherein the pharmacologically active agent is a vulnerary agent.

16. The method of claim 1, wherein the second polymer matrix comprises a photopolymerized poly(acrylate).

17. The method of claim 1, wherein the second polymer matrix comprises one or more monomers selected from the group consisting of α-acrylate-ω-acrylate-poly(alkylene glycol), trimethylolpropane triacrylate, and acrylic acid.

* * * * *

UNITED STATES PATENT AND TRADEMARK OFFICE
CERTIFICATE OF CORRECTION

PATENT NO.         : 8,025,901 B2
APPLICATION NO.    : 12/615859
DATED              : September 27, 2011
INVENTOR(S)        : Weiyuan John Kao et al.

It is certified that error appears in the above-identified patent and that said Letters Patent is hereby corrected as shown below:

In the Claims

Column 46, lines 20-24 – Cancel claim 12

Column 46, lines 25-26 – Cancel claim 13

Signed and Sealed this
Thirteenth Day of December, 2011

David J. Kappos
*Director of the United States Patent and Trademark Office*

UNITED STATES PATENT AND TRADEMARK OFFICE
CERTIFICATE OF CORRECTION

PATENT NO.        : 8,025,901 B2
APPLICATION NO.   : 12/615859
DATED             : September 27, 2011
INVENTOR(S)       : Weiyuan John Kao et al.

Page 1 of 2

It is certified that error appears in the above-identified patent and that said Letters Patent is hereby corrected as shown below:

Delete the title page and substitute therefore the attached title page showing the corrected number of claims in patent.

In the Claims

Column 46, lines 20-24 – Cancel claim 12

Column 46, lines 25-26 – Cancel claim 13

This certificate supersedes the Certificate of Correction issued December 13, 2011.

Signed and Sealed this
Tenth Day of January, 2012

David J. Kappos
*Director of the United States Patent and Trademark Office*

CERTIFICATE OF CORRECTION (continued)

(12) United States Patent
Kao et al.

(10) Patent No.: US 8,025,901 B2
(45) Date of Patent: Sep. 27, 2011

(54) BIFUNCTIONAL-MODIFIED HYDROGELS

(75) Inventors: Weiyuan John Kao, Middleton, WI (US); Jing Li, Madison, MN (US); David Lok, Madison, WI (US); Rathna Gundloori, Maharastra (IN)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/615,859

(22) Filed: Nov. 10, 2009

(65) Prior Publication Data

US 2010/0209509 A1     Aug. 19, 2010

Related U.S. Application Data

(63) Continuation of application No. 10/128,198, filed on Apr. 23, 2002, now Pat. No. 7,615,593.

(60) Provisional application No. 60/285,782, filed on Apr. 23, 2001.

(51) Int. Cl.
| | |
|---|---|
| A61K 35/00 | (2006.01) |
| A61K 9/10 | (2006.01) |
| A61K 47/48 | (2006.01) |
| C08G 81/00 | (2006.01) |
| C08L 101/00 | (2006.01) |
| C08L 101/14 | (2006.01) |

(52) U.S. Cl. ............ 424/484; 424/486; 514/772.1; 514/774; 435/177; 523/113; 530/815; 530/817

(58) Field of Classification Search ............ 424/484, 424/486; 514/772.1, 774; 435/177; 523/113; 530/815, 817
See application file for complete search history.

(56) References Cited

U.S. PATENT DOCUMENTS

| | | | |
|---|---|---|---|
| 4,390,519 A | 6/1983 | Sawyer | |
| 5,153,265 A | 10/1992 | Shadle et al. | |
| 5,672,662 A | 9/1997 | Harris et al. | |
| 5,847,089 A | 12/1998 | Damodaran et al. | |
| 5,863,984 A | 1/1999 | Doillon et al. | |
| 5,904,927 A | 5/1999 | Amiji | |
| 6,043,328 A | 3/2000 | Domschke et al. | |
| 6,129,761 A | 10/2000 | Hubbell | |
| 6,132,765 A | 10/2000 | DiCosmo et al. | |
| 6,258,351 B1 | 7/2001 | Harris | |
| 6,310,105 B1 | 10/2001 | Damodaran | |
| 6,323,278 B2 | 11/2001 | Rhee et al. | |
| 6,348,558 B1 * | 2/2002 | Harris et al. | 528/196 |
| 6,730,299 B1 | 5/2004 | Tayot et al. | |
| 6,818,018 B1 | 11/2004 | Sawhney | |
| 7,615,593 B2 | 11/2009 | Kao et al. | |
| 2005/0276858 A1 | 12/2005 | Kao et al. | |
| 2006/0100369 A1 | 5/2006 | Kao et al. | |

FOREIGN PATENT DOCUMENTS

| | | |
|---|---|---|
| EP | 747066 | 12/1996 |
| JP | 6-503840 | 4/1994 |
| JP | 8-231435 | 9/1996 |
| JP | 9-99052 | 4/1997 |
| JP | 10-085318 | 4/1998 |
| WO | WO 90/05755 | 5/1990 |
| WO | WO 93/00890 | 1/1993 |
| WO | WO 96/40304 | 12/1996 |
| WO | WO 96/40817 | 12/1996 |
| WO | WO 97/03106 | 1/1997 |
| WO | WO 97/22371 | 6/1997 |
| WO | WO 98/28364 | 7/1998 |
| WO | WO 98/46287 | 10/1998 |
| WO | WO 99/22770 | 5/1999 |
| WO | WO 00/78846 | 12/2000 |
| WO | WO 01/05443 | 1/2001 |
| WO | WO 02/085419 | 10/2002 |

OTHER PUBLICATIONS

Abuchowski et al., "Cancer therapy with chemically modified enzymes. I. Antitumor properties of polyethylene glycol—asparaginase conjugates," Cancer Biochem. Biophys. (1984) 7:175-186.

Andreopoulos, F.M. et al., "Photoimmobilization of organophosphorus hydrolase within a PEG-based hydrogel," Biotechnol. Bioeng. (1999) 65:579-588.

Brown et al., "The structure of propadienone," J. Am. Chem. Soc. (1985) 107:4109.

Bruson, "Cyanoethylation," Organic Reactions (1949) 5:79.

Buckmann et al., "Functionalization of poly(ethylene glycol) and monomethoxy-poly(ethylene glycol)," Markromol. Chem. (1981) 182:1379-1384.

Burmania et al., "Protein-based interpenetrating networks (IPN) for tissue scaffolds/drug release," (May 2, 2002).

Delgado et al., "The uses and properties of PEG-linked proteins," Crit. Rev. Ther. Drug Carrier System. (1992) 9:249.

Druniheller et al., "Densely crosslinked polymer networks of poly-(ethylene glycol) in trimethylolpropane triacrylate for cell-adhesion-resistant surfaces," J. Biomed. Mater. Res. (1995) 29:207.

D'Urso, E.M. et al., "Albumin-poly(ethylene glycol) hydrogel as matrix for enzyme immobilization: biochemical characterization of crosslinked acid phosphatase," Enz. Micro. Tech. (1996) 18:482-488.

Einerson et al., "Synthesis and physiochemical analysis of gelatin-based hydrogels for cell/drug carrier matrices," (May 2, 2002).

Fortier, "New polyethylene glycols for biomedical applications," Biotechnol. Genet. Eng. Rev. (1994) 12:329.

Harris et al., "Introduction to chemistry and biological applications of poly(ethylene glycol)," Am. Chem. Soc. Polymer Preprints (1989) 30:356.

Harris, J.M. et al., "Poly(ethylene glycol) chemistry and biological applications," Amer. Chemical Society, Washington, D.C. (1997) (Book).

(Continued)

*Primary Examiner* — Nathan M Nutter

(74) *Attorney, Agent, or Firm* — Foley & Lardner LLP

(57) ABSTRACT

Disclosed are hydrogels wherein a polymer matrix is modified to contain a bifunctional poly(alkylene glycol) molecule covalently bonded to the polymer matrix. The hydrogels can be cross-linked using, for example, glutaraldehyde. The hydrogels may also be crosslinked via an interpenetrating network of a photopolymerizable acrylates. The hydrogels may also be modified to have pharmacologically-active agents covalently bonded to the poly(alkylene glycol) molecules or entrained within the hydrogel. Living cells may also be entrained within the hydrogels.

15 Claims, 6 Drawing Sheets

SEQUENCE LISTING

<160> NUMBER OF SEQ ID NOS: 7

<210> SEQ ID NO 1
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 1

Arg Gly Asp
1

<210> SEQ ID NO 2
<211> LENGTH: 5

```
<212> TYPE: PRT
<213> ORGANISM: Artificial Sequence
<220> FEATURE:
<223> OTHER INFORMATION: Synthetic polypeptide

<400> SEQUENCE: 2

Pro His Ser Arg Asn
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 3

Gly Gly Gly Arg Gly Asp Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 4

Gly Gly Gly Pro His Ser Arg Asn Gly
1               5

<210> SEQ ID NO 5
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 5

Gly Gly Gly Arg Gly Asp Gly Gly Gly Gly Pro His Ser Arg
1               5                   10                  15

Asn Gly

<210> SEQ ID NO 6
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 6

Gly Gly Gly Pro His Ser Arg Asn Gly Gly Gly Gly Arg Gly
1               5                   10                  15

Asp Gly

<210> SEQ ID NO 7
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 7

Gly Gly Gly Arg Asp Gly Gly
1               5
```